United States Patent
Lundemose et al.

(10) Patent No.: US 10,449,245 B2
(45) Date of Patent: Oct. 22, 2019

(54) METHOD FOR REDUCING HIV-1 RESERVOIR SIZE USING MULTIVALENT IMMUNOGEN AND RESERVOIR PURGING AGENT

(71) Applicant: Bionor Immuno AS, Skien (NO)

(72) Inventors: Anker Lundemose, Oslo (NO); Mats Ökvist, Oslo (NO); Arnt Ove Hovden, Oslo (NO); Maja Sommerfelt Grønvold, Oslo (NO)

(73) Assignee: Bionor Immuno AS, Skien (NO)

( * ) Notice: Subject to any disclaimer, the term of this patent is extended or adjusted under 35 U.S.C. 154(b) by 0 days.

(21) Appl. No.: 15/114,296

(22) PCT Filed: Jan. 27, 2015

(86) PCT No.: PCT/EP2015/051627
§ 371 (c)(1),
(2) Date: Jul. 26, 2016

(87) PCT Pub. No.: WO2015/110665
PCT Pub. Date: Jul. 30, 2015

(65) Prior Publication Data
US 2017/0043009 A1 Feb. 16, 2017

(30) Foreign Application Priority Data
Jan. 27, 2014 (EP) .................................. 14152655

(51) Int. Cl.
| | |
|---|---|
| *A61K 39/21* | (2006.01) |
| *A61K 39/12* | (2006.01) |
| *A61K 38/15* | (2006.01) |
| *A61K 45/06* | (2006.01) |
| *A61K 31/4045* | (2006.01) |
| *A61K 31/454* | (2006.01) |
| *A61K 38/12* | (2006.01) |
| *A61K 38/18* | (2006.01) |
| *A61K 38/19* | (2006.01) |
| *A61K 38/20* | (2006.01) |
| *A61K 38/21* | (2006.01) |
| *G01N 33/569* | (2006.01) |
| *C12N 7/00* | (2006.01) |
| *A61K 39/00* | (2006.01) |

(52) U.S. Cl.
CPC .......... *A61K 39/21* (2013.01); *A61K 31/4045* (2013.01); *A61K 31/454* (2013.01); *A61K 38/12* (2013.01); *A61K 38/15* (2013.01); *A61K 38/18* (2013.01); *A61K 38/191* (2013.01); *A61K 38/20* (2013.01); *A61K 38/21* (2013.01); *A61K 39/12* (2013.01); *A61K 45/06* (2013.01); *C12N 7/00* (2013.01); *G01N 33/56988* (2013.01); *A61K 2039/545* (2013.01); *A61K 2039/55505* (2013.01); *A61K 2039/55522* (2013.01); *A61K 2039/55566* (2013.01); *A61K 2039/55572* (2013.01); *A61K 2039/70* (2013.01); *C12N 2740/16034* (2013.01); *C12N 2740/16234* (2013.01); *C12N 2740/16271* (2013.01); *G01N 2333/16* (2013.01); *G01N 2469/20* (2013.01)

(58) Field of Classification Search
CPC ..... A61K 39/21; A61K 38/15; A61K 2039/70
See application file for complete search history.

(56) References Cited

FOREIGN PATENT DOCUMENTS

| | | |
|---|---|---|
| WO | WO 00/52040 A1 | 9/2000 |
| WO | WO 2013/182660 A1 | 12/2013 |

OTHER PUBLICATIONS

Rasmussen, T. A., et al., Feb. 2016, Reversal of latency as part of a cure for HIV-1, Trends in Microbiol. 24(2):90-97.*
Shan, L., and R. F. Siliciano, 2013, From reactivation of latent HIV-1 to elimination of the latent reservoir: The presences of multiple barriers to viral eradication, Bioessays 35:544-552.*
Pollard, R. B., et al., Apr. 2014, Safety and efficacy of the peptide-based therapeutic vaccine for HIV-1, Vacc-4x: a phase 2 randomised, duble-blind placebo-controlled trial, The Lancet Infect. Dis. 14:291-300.*
Xing, S., and R. F. Siliciano, Jun. 2013, Targeting HIV latency: pharmacologic strategies toward eradication, Drug Discovery Today 18(11/12):541-551.*
Barouch, D. H., Oct. 2008, Challenges in the development of an HIV-1 vaccine, Nature 455:613-619.*
Walker, B. D., and D. R. Burton, May 2008, Toward an AIDS vaccine, Science 320:760-764.*
Kran, A,-M. B., et al., 2004, HLA- and Dose-dependent Immunogenicity of a Peptide-based HIV-1 Immunotherapy Candidate (Vacc-4x), AIDS 18:1875-1883.*
Bullen, C. K., et al., Apr. 2014, New Ex Vivo Approaches Distinguish Effective and Ineffective Single Agents for Reversing HIV-1 latency In Vivo, Nat. Med. 20(4):425-430.*
Sogaard, O. S., et al., Sep. 2015, The Depsipeptide Romidepsin Reverses HIV-1 Latency In Vivo, PLoS Pathog 11(9): e1005142 pp. 1-22.*
"Report —Clinical data phase II," 2005, pp. 1-10, internet citation retrieved from the Internet, 2013: https://register.epo.org/application?number+EP00911492&Ing=en&tab=doclist.
Jones, R., et al., "Histone Deacetylase Inhibitors Impair the Elimination of Hiv-Infected Cells by Cytotoxic T-Lymphocytes," *PLOS Pathogens*, 2014, vol. 10(8), pp. 1-19.
Lind, A., et al., "Boosters of a therapeutic HIV-1 vaccine induce divergent T cell responses related to regulatory mechanisms," *Vaccine*, 2013, vol. 31(41), pp. 4611-4618.
Lundemose, A., et al., "Third Quarter Results 2013," 2013, BionorPharma, pp. 1-27; retrieved from the Internet, 2014: URL:http://www.bionorpharma.com/filestore/Q3_2013Presentation.pdf.

(Continued)

*Primary Examiner* — Jeffrey S Parkin
(74) *Attorney, Agent, or Firm* — Womble Bond Dickinson (US) LLP

(57) ABSTRACT

The present invention relates to novel compositions of active agents and methods for the treatment of HIV infection and AIDS. In particular, the present invention relates to novel methods for treatment of HIV infection and prevention of AIDS.

17 Claims, No Drawings
Specification includes a Sequence Listing.

(56) References Cited

OTHER PUBLICATIONS

Lundemose, A., et al., "Exporing the Path Towards a Functional Cure for HIV," BionorPharma, 2013, pp. 1-27, retrieved from the Internet 2014: URL:http://www.bionorpharma.com/filestore/BionorNov2013.pdf.

Pollard, R., et al., "Safety and efficacy of the peptide-based therapeutic vaccine for HIV-1, Vacc-4x: a phase 2 randomised, double-blind, placebo-controlled trial," *The Lancet Infectious Diseases*, 2014, vol. 14(4), pp. 291-300.

Rasmussen, T., et al., "Eliminating the latent HIV reservoir by reactivation strategies," *Human Vaccines & Immunotherapeutics*, 2013, vol. 9(4), pp. 1-10.

Rasmussen, T., et al., "Comparison of HDAC inhibitors in clinical development," *Human Vaccines & Immunotherapies*, 2013, vol. 9(5), pp. 993-1001.

Roine, Synne H., "Bionor Pharma's Kick, Kill & Boost" Strategy Advances—Romidepsin Chosen as the "Kick," *FirstWord Pharma*, 2013, 2 pages; retrieved from The Internet 2015: URL:http://www.firstwordpharma.com/node/1138165#axzz3VIFSGteC.

Wightman, F., et al., "HDAC inhibitor in HIV," *Immunology and Cell Biology*, 2012, vol. 90(1), pp. 47-54.

\* cited by examiner

SEQUENCE LISTING

```
<160> NUMBER OF SEQ ID NOS: 22

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Lys or Arg
<220> FEATURE:
<221> NAME/KEY: MISC_FEATURE
<222> LOCATION: (2)..(2)
<223> OTHER INFORMATION: Xaa in position 2 is Ala, Gly, Ser or Arg
<220> FEATURE:
<221> NAME/KEY: MISC_FEATURE
<222> LOCATION: (3)..(3)
<223> OTHER INFORMATION: Xaa in position 3 is Leu or Met
<220> FEATURE:
<221> NAME/KEY: MISC_FEATURE
<222> LOCATION: (4)..(4)
<223> OTHER INFORMATION: Xaa in position 4 is Gly or Arg
<220> FEATURE:
<221> NAME/KEY: MISC_FEATURE
<222> LOCATION: (5)..(5)
<223> OTHER INFORMATION: Xaa in position 5 is Pro, Thr, Val, Ser, Gln or
      Ala
<220> FEATURE:
<221> NAME/KEY: MISC_FEATURE
<222> LOCATION: (6)..(6)
<223> OTHER INFORMATION: Xaa in position 6 is Gly, Ala, Lys, Arg, Gln or
      Glu
<220> FEATURE:
<221> NAME/KEY: MISC_FEATURE
<222> LOCATION: (8)..(8)
<223> OTHER INFORMATION: Xaa in position 8 is Thr or Ser
<220> FEATURE:
<221> NAME/KEY: MISC_FEATURE
<222> LOCATION: (9)..(9)
<223> OTHER INFORMATION: Xaa in position 9 is Leu or Ile
<220> FEATURE:
<221> NAME/KEY: MISC_FEATURE
<222> LOCATION: (14)..(14)
<223> OTHER INFORMATION: Xaa in position 14 is Thr, Ser or Val
<220> FEATURE:
<221> NAME/KEY: MISC_FEATURE
<222> LOCATION: (15)..(15)
<223> OTHER INFORMATION: Xaa in position 15 is Ala or Ser
<220> FEATURE:
<221> NAME/KEY: MISC_FEATURE
<222> LOCATION: (16)..(16)
```

```
<223> OTHER INFORMATION: Xaa in position 16 is Cys or Ser
<220> FEATURE:
<221> NAME/KEY: MISC_FEATURE
<222> LOCATION: (17)..(17)
<223> OTHER INFORMATION: Xaa in position 17 is Gln or Leu
<220> FEATURE:
<221> NAME/KEY: MISC_FEATURE
<222> LOCATION: (18)..(18)
<223> OTHER INFORMATION: Xaa in position 18 is Gly, Glu or Arg
<220> FEATURE:
<221> NAME/KEY: MISC_FEATURE
<222> LOCATION: (20)..(20)
<223> OTHER INFORMATION: Xaa in position 20 is Gly or Arg

<400> SEQUENCE: 1

Xaa Xaa Xaa Xaa Xaa Xaa Ala Xaa Xaa Gln Thr Pro Trp Xaa Xaa Xaa
1               5                   10                  15

Xaa Xaa Val Xaa
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Lys Ala Leu Gly Pro Gly Ala Thr Leu Gln Thr Pro Trp Thr Ala Cys
1               5                   10                  15

Gln Gly Val Gly
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Arg Ala Leu Gly Pro Ala Ala Thr Leu Gln Thr Pro Trp Thr Ala Ser
1               5                   10                  15

Leu Gly Val Gly
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Arg, Lys, Asp or none
<220> FEATURE:
<221> NAME/KEY: MISC_FEATURE
<222> LOCATION: (2)..(2)
<223> OTHER INFORMATION: Xaa in position 2 is Trp, Gly, Lys or Arg
<220> FEATURE:
<221> NAME/KEY: MISC_FEATURE
<222> LOCATION: (3)..(3)
<223> OTHER INFORMATION: Xaa in position 3 is Ile, Leu, Val or Met
<220> FEATURE:
<221> NAME/KEY: MISC_FEATURE
<222> LOCATION: (4)..(4)
<223> OTHER INFORMATION: Xaa in position 4 is Ile, Val or Leu
<220> FEATURE:
<221> NAME/KEY: MISC_FEATURE
```

```
<222> LOCATION: (5)..(5)
<223> OTHER INFORMATION: Xaa in position 5 Leu, Met, Val or Pro
<220> FEATURE:
<221> NAME/KEY: MISC_FEATURE
<222> LOCATION: (12)..(12)
<223> OTHER INFORMATION: Xaa in position 12 is  0, 1, 2 or 3 Gly
      residues
<220> FEATURE:
<221> NAME/KEY: MISC_FEATURE
<222> LOCATION: (13)..(13)
<223> OTHER INFORMATION: Xaa in position 13 is Arg or Lys
<220> FEATURE:
<221> NAME/KEY: MISC_FEATURE
<222> LOCATION: (14)..(14)
<223> OTHER INFORMATION: Xaa in position 14 is Met or Leu
<220> FEATURE:
<221> NAME/KEY: MISC_FEATURE
<222> LOCATION: (16)..(16)
<223> OTHER INFORMATION: Xaa in position 16 is Ser, Cys or Gln
<220> FEATURE:
<221> NAME/KEY: MISC_FEATURE
<222> LOCATION: (18)..(18)
<223> OTHER INFORMATION: Xaa in position 18 is Thr, Val, Ile, Ser or Ala
<220> FEATURE:
<221> NAME/KEY: MISC_FEATURE
<222> LOCATION: (19)..(19)
<223> OTHER INFORMATION: Xaa in position 19 is Ser, Gly or Thr
<220> FEATURE:
<221> NAME/KEY: MISC_FEATURE
<222> LOCATION: (22)..(22)
<223> OTHER INFORMATION: Xaa in position 22 is Asp, Glu, Cys or Gly
<220> FEATURE:
<221> NAME/KEY: MISC_FEATURE
<222> LOCATION: (23)..(23)
<223> OTHER INFORMATION: Xaa in position 22 is Gly or none

<400> SEQUENCE: 4

Xaa Xaa Xaa Xaa Xaa Gly Leu Asn Pro Leu Val Xaa Xaa Xaa Tyr Xaa
1               5                   10                  15

Pro Xaa Xaa Ile Leu Xaa Xaa
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic peptide

<400> SEQUENCE: 5

Trp Ile Ile Pro Gly Leu Asn Pro Leu Val Gly Gly Gly Lys Leu Tyr
1               5                   10                  15

Ser Pro Thr Ser Ile Leu Cys Gly
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic peptide

<400> SEQUENCE: 6

Arg Trp Leu Leu Leu Gly Leu Asn Pro Leu Val Gly Gly Gly Arg Leu
1               5                   10                  15

Tyr Ser Pro Thr Ser Ile Leu Gly
            20

<210> SEQ ID NO 7
<211> LENGTH: 23
```

```
<212> TYPE: PRT
<213> ORGANISM: Artificial Sequence
<220> FEATURE:
<223> OTHER INFORMATION: Synthetic peptide

<400> SEQUENCE: 7

Lys Ile Leu Leu Gly Leu Asn Pro Leu Val Gly Gly Gly Arg Leu Tyr
1               5                   10                  15

Ser Pro Thr Ser Ile Leu Gly
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic peptide

<400> SEQUENCE: 8

Arg Leu Leu Leu Gly Leu Asn Pro Leu Val Gly Gly Gly Arg Leu Tyr
1               5                   10                  15

Ser Pro Thr Thr Ile Leu Gly
            20

<210> SEQ ID NO 9
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Asn, Ser, Gly, His, Ala,
      Pro, Arg or none
<220> FEATURE:
<221> NAME/KEY: MISC_FEATURE
<222> LOCATION: (2)..(2)
<223> OTHER INFORMATION: Xaa in position 2 is Asn, Ala or Lys
<220> FEATURE:
<221> NAME/KEY: MISC_FEATURE
<222> LOCATION: (3)..(3)
<223> OTHER INFORMATION: Xaa in position 3 is Pro, Gln, Gly, Ile or Leu
<220> FEATURE:
<221> NAME/KEY: MISC_FEATURE
<222> LOCATION: (7)..(7)
<223> OTHER INFORMATION: Xaa in position 7 is Val or Ala
<220> FEATURE:
<221> NAME/KEY: MISC_FEATURE
<222> LOCATION: (8)..(8)
<223> OTHER INFORMATION: Xaa in position 8 is Gly or Lys
<220> FEATURE:
<221> NAME/KEY: MISC_FEATURE
<222> LOCATION: (9)..(9)
<223> OTHER INFORMATION: Xaa in position 9 is Glu, Asp, Lys, Phe or Thr
<220> FEATURE:
<221> NAME/KEY: MISC_FEATURE
<222> LOCATION: (10)..(10)
<223> OTHER INFORMATION: Xaa in position 10 is Ile, Met, Val or Leu
<220> FEATURE:
<221> NAME/KEY: MISC_FEATURE
<222> LOCATION: (11)..(11)
<223> OTHER INFORMATION: Xaa in position 11 is Tyr, Leu or none
<220> FEATURE:
<221> NAME/KEY: MISC_FEATURE
<222> LOCATION: (12)..(12)
<223> OTHER INFORMATION: Xaa in position 12 is Ser or none
<220> FEATURE:
<221> NAME/KEY: MISC_FEATURE
<222> LOCATION: (13)..(13)
<223> OTHER INFORMATION: Xaa in position 13 is 1, 2 or 3 Gly residues
<220> FEATURE:
<221> NAME/KEY: MISC_FEATURE
```

```
<222> LOCATION: (14)..(14)
<223> OTHER INFORMATION: Xaa in position 14 is Arg or none
<220> FEATURE:
<221> NAME/KEY: MISC_FEATURE
<222> LOCATION: (15)..(15)
<223> OTHER INFORMATION: Xaa in position 15 is Asp, Arg, Trp, Ala or
      none
<220> FEATURE:
<221> NAME/KEY: MISC_FEATURE
<222> LOCATION: (16)..(16)
<223> OTHER INFORMATION: Xaa in position 16 is Ile or none
<220> FEATURE:
<221> NAME/KEY: MISC_FEATURE
<222> LOCATION: (17)..(17)
<223> OTHER INFORMATION: Xaa in position 17 is Tyr or none
<220> FEATURE:
<221> NAME/KEY: MISC_FEATURE
<222> LOCATION: (18)..(18)
<223> OTHER INFORMATION: Xaa in position 18 is Lys or Arg
<220> FEATURE:
<221> NAME/KEY: MISC_FEATURE
<222> LOCATION: (19)..(19)
<223> OTHER INFORMATION: Xaa in position 19 is Arg, Lys or Asp
<220> FEATURE:
<221> NAME/KEY: MISC_FEATURE
<222> LOCATION: (20)..(20)
<223> OTHER INFORMATION: Xaa in position 20 is Trp or Gly
<220> FEATURE:
<221> NAME/KEY: MISC_FEATURE
<222> LOCATION: (21)..(21)
<223> OTHER INFORMATION: Xaa in position 21 is Ile, Met, Val, Gln or Ala
<220> FEATURE:
<221> NAME/KEY: MISC_FEATURE
<222> LOCATION: (22)..(22)
<223> OTHER INFORMATION: Xaa in position 22 is Ile, Val or Ala
<220> FEATURE:
<221> NAME/KEY: MISC_FEATURE
<222> LOCATION: (23)..(23)
<223> OTHER INFORMATION: Xaa in position 23 is Leu, Met or Val
<220> FEATURE:
<221> NAME/KEY: MISC_FEATURE
<222> LOCATION: (24)..(24)
<223> OTHER INFORMATION: Xaa in position 24 is Gly or Cys
<220> FEATURE:
<221> NAME/KEY: MISC_FEATURE
<222> LOCATION: (25)..(25)
<223> OTHER INFORMATION: Xaa in position 25 is Leu or none

<400> SEQUENCE: 9

Xaa Xaa Xaa Pro Ile Pro Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic peptide

<400> SEQUENCE: 10

Arg Asn Ile Pro Ile Pro Val Gly Asp Ile Tyr Gly Gly Gly Asp Ile
1               5                   10                  15

Tyr Lys Arg Trp Gln Ala Leu Cys Leu
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic peptide
```

<400> SEQUENCE: 11

Arg Ala Ile Pro Ile Pro Ala Gly Thr Leu Leu Ser Gly Gly Gly Arg
1               5                   10                  15

Ala Ile Tyr Lys Arg Trp Ala Ile Leu Gly
            20                  25

<210> SEQ ID NO 12
<211> LENGTH: 23
<212> TYPE: PRT
<213> ORGANISM: Artificial Sequence
<220> FEATURE:
<223> OTHER INFORMATION: Synthetic peptide

<400> SEQUENCE: 12

Ala Leu Pro Ile Pro Ala Gly Phe Ile Tyr Gly Gly Gly Arg Ile Tyr
1               5                   10                  15

Lys Arg Trp Gln Ala Leu Gly
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic peptide

<400> SEQUENCE: 13

Lys Ile Pro Ile Pro Val Gly Phe Ile Gly Gly Gly Trp Ile Tyr Lys
1               5                   10                  15

Arg Trp Ala Ile Leu Gly
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic peptide

<400> SEQUENCE: 14

Lys Ile Pro Ile Pro Val Gly Thr Leu Leu Ser Gly Gly Gly Arg Ile
1               5                   10                  15

Tyr Lys Arg Trp Ala Ile Leu Gly
            20

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Pro, Lys, Arg or none
<220> FEATURE:
<221> NAME/KEY: MISC_FEATURE
<222> LOCATION: (2)..(2)
<223> OTHER INFORMATION: Xaa in position 2 is Glu, Arg, Phe or Lys
<220> FEATURE:
<221> NAME/KEY: MISC_FEATURE
<222> LOCATION: (5)..(5)
<223> OTHER INFORMATION: Xaa in position 5 is Pro or Thr
<220> FEATURE:
<221> NAME/KEY: MISC_FEATURE
<222> LOCATION: (6)..(6)

```
<223> OTHER INFORMATION: Xaa in position 6 is Met, Thr or Nleu
<220> FEATURE:
<221> NAME/KEY: MISC_FEATURE
<222> LOCATION: (7)..(7)
<223> OTHER INFORMATION: Xaa in position 7 is Phe or Leu
<220> FEATURE:
<221> NAME/KEY: MISC_FEATURE
<222> LOCATION: (8)..(8)
<223> OTHER INFORMATION: Xaa in position 8 is Ser, Thr, Ala or Met
<220> FEATURE:
<221> NAME/KEY: MISC_FEATURE
<222> LOCATION: (9)..(9)
<223> OTHER INFORMATION: Xaa in position 9 is Ala, Glu or Leu
<220> FEATURE:
<221> NAME/KEY: MISC_FEATURE
<222> LOCATION: (11)..(11)
<223> OTHER INFORMATION: Xaa in position 11 is Ser or none
<220> FEATURE:
<221> NAME/KEY: MISC_FEATURE
<222> LOCATION: (12)..(12)
<223> OTHER INFORMATION: Xaa in position 12 is 1, 2 or 3 Gly residues
<220> FEATURE:
<221> NAME/KEY: MISC_FEATURE
<222> LOCATION: (13)..(13)
<223> OTHER INFORMATION: Xaa in position 12 is 0, 1, 2 or 3 Arg residues
<220> FEATURE:
<221> NAME/KEY: MISC_FEATURE
<222> LOCATION: (14)..(14)
<223> OTHER INFORMATION: Xaa in position 14 is Ala, Arg or none
<220> FEATURE:
<221> NAME/KEY: MISC_FEATURE
<222> LOCATION: (15)..(15)
<223> OTHER INFORMATION: Xaa in position 15 is Ile, Leu or none
<220> FEATURE:
<221> NAME/KEY: MISC_FEATURE
<222> LOCATION: (16)..(16)
<223> OTHER INFORMATION: Xaa in position 16 is Ser, Ala, Leu or none
<220> FEATURE:
<221> NAME/KEY: MISC_FEATURE
<222> LOCATION: (17)..(17)
<223> OTHER INFORMATION: Xaa in position 17 is Tyr, Glu or Asp
<220> FEATURE:
<221> NAME/KEY: MISC_FEATURE
<222> LOCATION: (18)..(18)
<223> OTHER INFORMATION: Xaa in position 18 is Gly or Asp
<220> FEATURE:
<221> NAME/KEY: MISC_FEATURE
<222> LOCATION: (19)..(19)
<223> OTHER INFORMATION: Xaa in position 19 is Ala or Leu
<220> FEATURE:
<221> NAME/KEY: MISC_FEATURE
<222> LOCATION: (20)..(20)
<223> OTHER INFORMATION: Xaa in position 20 is Thr, Ile, Val, Leu or Asn
<220> FEATURE:
<221> NAME/KEY: MISC_FEATURE
<222> LOCATION: (21)..(21)
<223> OTHER INFORMATION: Xaa in position 21 is Pro, Thr or Ser
<220> FEATURE:
<221> NAME/KEY: MISC_FEATURE
<222> LOCATION: (22)..(22)
<223> OTHER INFORMATION: Xaa in position 22 is Tyr, Phe, Nleu, His or
      Gln
<220> FEATURE:
<221> NAME/KEY: MISC_FEATURE
<222> LOCATION: (23)..(23)
<223> OTHER INFORMATION: Xaa in position 23 is Asp, Asn, Leu or Ala
<220> FEATURE:
<221> NAME/KEY: MISC_FEATURE
<222> LOCATION: (24)..(24)
<223> OTHER INFORMATION: Xaa in position 24 is Leu, Ile, Val or Asn
<220> FEATURE:
<221> NAME/KEY: MISC_FEATURE
<222> LOCATION: (25)..(25)
<223> OTHER INFORMATION: Xaa in position 25 is Asn, Tyr, Cys or Gly
<220> FEATURE:
<221> NAME/KEY: MISC_FEATURE
<222> LOCATION: (26)..(26)
<223> OTHER INFORMATION: Xaa in position 26 is Thr, Met, Ile, Ala, Val
      or none
```

```
<220> FEATURE:
<221> NAME/KEY: MISC_FEATURE
<222> LOCATION: (27)..(27)
<223> OTHER INFORMATION: Xaa in postion 27 is Gly or none

<400> SEQUENCE: 15

Xaa Xaa Ile Ile Xaa Xaa Xaa Xaa Xaa Leu Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa in position 6 is Norleucine
<220> FEATURE:
<221> NAME/KEY: MISC_FEATURE
<222> LOCATION: (21)..(21)
<223> OTHER INFORMATION: Xaa in position 21 is Norleucine

<400> SEQUENCE: 16

Lys Phe Ile Ile Pro Xaa Phe Ser Ala Leu Gly Gly Ala Ile Ser Tyr
1               5                   10                  15

Asp Leu Asn Thr Xaa Leu Asn Cys Ile
            20                  25

<210> SEQ ID NO 17
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa in position 6 is Norleucine

<400> SEQUENCE: 17

Lys Phe Ile Ile Pro Xaa Phe Ser Ala Leu Ser Gly Gly Gly Ala Ile
1               5                   10                  15

Ser Tyr Asp Leu Asn Thr Phe Leu Asn Cys Ile Gly
            20                  25

<210> SEQ ID NO 18
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa in position 6 is Norleucine

<400> SEQUENCE: 18

Arg Phe Ile Ile Pro Xaa Phe Thr Ala Leu Ser Gly Gly Arg Arg Ala
1               5                   10                  15

Leu Leu Tyr Gly Ala Thr Pro Tyr Ala Ile Gly
            20                  25

<210> SEQ ID NO 19
```

```
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa in position 5 is Norleucine

<400> SEQUENCE: 19

Lys Ile Ile Pro Xaa Phe Ser Ala Leu Gly Gly Gly Arg Leu Leu Tyr
1               5                   10                  15

Gly Ala Thr Pro Tyr Ala Ile Gly
            20

<210> SEQ ID NO 20
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa in position 5 is Norleucine

<400> SEQUENCE: 20

Arg Ile Ile Pro Xaa Phe Thr Ala Leu Ser Gly Gly Gly Arg Leu Leu
1               5                   10                  15

Tyr Gly Ala Thr Pro Tyr Ala Ile Gly
            20                  25

<210> SEQ ID NO 21
<211> LENGTH: 24
<212> TYPE: PRT
<213> ORGANISM: Artificial Sequence
<220> FEATURE:
<223> OTHER INFORMATION: Synthetic peptide

<400> SEQUENCE: 21

Asn Ile Pro Ile Pro Val Gly Asp Ile Tyr Gly Gly Gly Asp Ile Tyr
1               5                   10                  15

Lys Arg Trp Gln Ala Leu Cys Leu
            20

<210> SEQ ID NO 22
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa in position 5 is Norleucine
<220> FEATURE:
<221> NAME/KEY: MISC_FEATURE
<222> LOCATION: (20)..(20)
<223> OTHER INFORMATION: Xaa in position 20 is Norleucine

<400> SEQUENCE: 22

Trp Ile Ile Pro Xaa Phe Ser Ala Leu Gly Gly Ala Ile Ser Tyr Asp
1               5                   10                  15

Leu Asn Thr Xaa Leu Asn Cys Ile
            20
```

METHOD FOR REDUCING HIV-1 RESERVOIR SIZE USING MULTIVALENT IMMUNOGEN AND RESERVOIR PURGING AGENT

CROSS-REFERENCE TO RELATED APPLICATIONS

This application is a national stage filing under 35 U.S.C. 371 of PCT/EP2015/051627, filed Jan. 27, 2015, which International Application was published by the International Bureau in English on Jul. 30, 2015, and application claims priority from European Application No. 14152655.8, filed Jan. 27, 2014.

FIELD OF THE INVENTION

The present invention relates to a novel dosage regimen in the treatment of HIV infections and AIDS. in particular, the present invention relates to a specific novel use of formulations of HIV-specific vaccine peptides administered in a dosis regimen together with a a reservoir purging agent. The formulations may further be administered with other therapeutic agents, such as in combination with immunomodulatory compounds and/or other reservoir purging agents, such as histone deacetylase (HDAC) inhibitors.

BACKGROUND OF THE INVENTION

HIV-1 infection is today perceived as an incurable chronic viral infection in which lifelong combination antiretroviral therapy (cART) is needed to avoid disease (Egger, Hirschel et al. 1997, Palella, Delaney et al. 1998). Very early during acute HIV infection a latent reservoir is established and despite effective cART, HIV-1 persists in latently infected cells (Dai, Agosto et al. 2009, Carter, Onafuwa-Nuga et al. 2010, Wightman, Solomon et al. 2010). Upon treatment interruption, the virus quickly replicates, and viremia rebounds to pre-treatment levels. In the inactive, resting state latently infected cells are unrecognizable to the immune system and unresponsive to antiretroviral drugs (Chun, Stuyver et al. 1997, Finzi, Hermankova et al. 1997). The size of the reservoir likely varies between individuals and may be influenced by a number of different factors such as host immune constitution, time from diagnosis to initiation, level of persistent immune activation, antiretroviral treatment regimens used and individual response to treatment. Earlier studies employing viral outgrowth assays indicated that the number of latent CD4 T cells harboring replication-competent virus was approximately 1 per $10^6$ cells.

A broad range of bioanalytical assays have been used in the attempt to quantify the reservoir but it is currently unclear which assay(s) should be used to monitor HIV-1 reservoirs in clinical studies of eradication strategies (Eriksson, Graf et al. 2013). Upon activation, resting T cells carrying replication competent integrated proviral DNA are capable of resuming HIV transcription (Chun, Finzi et al. 1995, Chun, Carruth et al. 1997, Eriksson, Graf et al. 2013). One of the proposed ways of curing HIV-1 is to activate and kill latently infected cells in the presence of antiretroviral therapy (Deeks 2012). Epigenetic modulation of the molecular mechanisms that block transcription of integrated HIV DNA can reactivate HIV-1 expression in resting infected memory CD4 T cells and disrupt latency (Rasmussen, Schmeltz Sogaard et al. 2013, Rasmussen, Tolstrup et al. 2013). Histone deacetylase inhibitors (HDACi) turn on genes by promoting acetylation of lysine residues on histones (Van Lint, Emiliani et al. 1996, Tyagi, Pearson et al. 2010). This induces chromatin relaxation and transcriptional activation. The HDACi romidepsin (Celgene) potently activates HIV-1 expression in latently infected cell lines and primary T cells (Geleziunas 2013).

Vacc-4x is a peptide-based HIV-1 therapeutic vaccine that aims to improve immune responses to p24Gag since this has been associated with slower disease progression and improved virus control (Kiepiela 2007; Zuniga 2006). The primary objective of Vacc-4x immunization is to strengthen the immune system's response to HIV p24. The enhanced immune response to HIV-1 following immunization with Vacc-4x could improve the host immune system as part of an HIV functional cure treatment strategy.

In one of the largest randomized, placebo controlled HIV therapeutic vaccine trials conducted to date (study CT-BI/Vacc-4x/2007/1), Vacc-4x and rhuGM-CSF (Leukine®) as adjuvant showed a significant reduction in viral load (VL) set point in the Vacc-4x group as compared to placebo and a significant reduction in VL set point from historic preART values, despite higher preART values being present in the Vacc-4x group as compared to placebo. Additionally Vacc-4x was shown to be immunogenic, inducing proliferative responses in both CD4 and CD8 T-cell New HIV p24 peptides are described in WO91/13360, wherein the peptides are used in a method of discriminating between a false and true diagnosed HIV-positive serum sample.

Johnson R. P., et al., The Journal of Immunology, Vol. 147, p. 1512-1521, No. 5, Sep. 1, 1991 describe an analysis of the fine specificity of gag-specific CTL-responses in three HIV-1 seropositive individuals, the gag-specific CTL-responses were found to be mediated by CD3+CD8+ lymphocytes which are HLA class I restricted.

EP-A-0 356 007 discloses antigenic determinants, in particular it relates to synthetic polypeptide sequences which are related to proteins present in the HIV-1 and which can be used as a basis for a potential vaccine against AIDS.

Rosenberg E. S. et al., Science, Vol. 278, 21 Nov. 1997, p. 1447-1450 describe that virus specific CD4+ T helper lymphocytes are critical to the maintenance of effective immunity in a number of chronic viral infections, but are characteristically undetectable in chronic human immunodeficiency virus-type 1 (HIV-1) infection. HIV-1-specific proliferative responses to p24 were inversely related to viral load. They conclude that the HIV-1-specific helper cells are likely to be important in immunotherapeutic interventions and vaccine development.

EP 0 230 222, EP 0 270 114, DE 37 11 016 and GB 2 188 639 all in the name of F. Hoffmann-La Roche & Co. Aktiengesellschaft concern recombinant expression and purification of an HTLVIII Gag/Env gene protein or fusion proteins. The proteins consisting of native sequences can be purified to homogeneity and used as a basis for diagnostic tests for detection of antibodies against viruses associated with AIDS. The gag/env protein may also be formulated for use as a vaccine for protection against AIDS through prophylactic immunization.

International Patent Application WO00/52040 discloses methods for treating HIV infections by administering e.g. HIV specific peptides based on conserved regions of HIV gag p24.

There is a need to provide improved treatment dosis regimens for the treatment of HIV infections and AIDS.

OBJECT OF THE INVENTION

It is an object of embodiments of the invention to provide effective methods, which can be used in the treatment and/or prevention of HIV infection and AIDS.

The present invention is based on the finding that HIV-specific vaccine peptides may be used in specific dosage regimens together with specific reservoir purging agents, providing an effective method in the treatment and/or eradication of HIV infection and AIDS. Such specific dosage regimens may also provide other advantageous effects particularly in relation to the properties of pharmaceutical compositions when formulated as a combination therapy.

SUMMARY OF THE INVENTION

It has been found that HIV-specific vaccine peptides administered in a specific dosage regimen together with specific reservoir purging agents will provide much better treatments.

So, in a first aspect of the present invention is provided a method for reducing and/or delaying pathological effects of human immunodeficiency virus I (HIV) or for reducing the risk of developing acquired immunodeficiency syndrome (AIDS) in a human infected with HIV, the method comprising the steps of:

a) a therapeutic HIV-1 immunization phase consisting of the administering in one or more doses of an effective amount of one or more HIV-specific peptide selected from the list consisting of the amino acid sequence shown in SEQ ID NO: 18 (Vacc-10), SEQ ID NO: 11 (Vacc-11), SEQ ID NO: 6 (Vacc-12), and SEQ ID NO: 3 (Vacc-13) over a period of 1-12 weeks; and b) a subsequent viral reactivation phase consisting of the administering of an effective amount of a reservoir purging agent.

In a second aspect of the present invention is provided a kit for reducing and/or delaying pathological effects of human immunodeficiency virus I (HIV) or for reducing the risk of developing acquired immunodeficiency syndrome (AIDS) in a human infected with HIV, which kit comprises a) one or more doses of an effective amount of one or more HIV-specific peptide selected from the list consisting of the amino acid sequence shown in SEQ ID NO: 18 (Vacc-10), SEQ ID NO: 11 (Vacc-11), SEQ ID NO: 6 (Vacc-12), and SEQ ID NO: 3 (Vacc-13) over a period of 1-12 weeks; and b) a reservoir purging agent, optionally c) one or more further therapeutically active agent.

In a third aspect of the present invention there is provided a method for reducing and/or delaying pathological effects of human immunodeficiency virus I (HIV) or for reducing the risk of developing acquired immunodeficiency syndrome (AIDS) in a human infected with HIV, the method comprising the steps of:

a) a therapeutic HIV-1 immunization phase consisting of the administering in one or more doses of an effective amount of one or more HIV-specific peptide selected from the group of amino acid sequences:

$Xaa_1$ $Xaa_2$ $Xaa_3$ $Xaa_4$ $Xaa_5$ $Xaa_6$ Ala $Xaa_8$ $Xaa_9$ Gln Thr Pro Trp $Xaa_{14}$ $Xaa_{15}$ $Xaa_{16}$ $Xaa_{17}$ $Xaa_{18}$ Val $Xaa_{20}$ (SEQ ID NO: 1);

wherein Xaa in position 1 is Lys or Arg,
Xaa in position 2 is Ala, Gly, Ser or Arg,
Xaa in position 3 is Leu or Met,
Xaa in position 4 is Gly or Arg,
Xaa in position 5 is Pro, Thr, Val, Ser, Gln or Ala,
Xaa in position 6 is Gly, Ala, Lys, Arg, Gln or Glu,
Xaa in position 8 is Thr or Ser,
Xaa in position 9 is Leu or Ile,
Xaa in position 14 is Thr, Ser or Val,
Xaa in position 15 is Ala or Ser,
Xaa in position 16 is Cys or Ser,
Xaa in position 17 is Gln or Leu,
Xaa in position 18 is Gly, Glu or Arg, and
Xaa in position 20 is Gly or Arg;

$Xaa_1$ $Xaa_2$ $Xaa_3$ $Xaa_4$ $Xaa_5$ Gly Leu Asn Pro Leu Val $[Gly]_n$ $Xaa_{12}$ $Xaa_{13}$ Tyr $Xaa_{15}$ Pro $Xaa_{17}$ $Xaa_{18}$ Ile Leu $Xaa_{21}$ $Xaa_{22}$ (SEQ ID NO: 4);

wherein Xaa in position 1 is Arg, Lys, Asp or none,
Xaa in position 2 is Trp, Gly, Lys or Arg,
Xaa in position 3 is Ile, Leu, Val or Met,
Xaa in position 4 is Ile, Val or Leu,
Xaa in position 5 Leu, Met, Val or Pro,
Xaa in position 12 is Arg or Lys,
Xaa in position 13 is Met or Leu,
Xaa in position 15 is Ser, Cys or Gln,
Xaa in position 17 is Thr, Val, Ile, Ser or Ala,
Xaa in position 18 is Ser, Gly or Thr,
Xaa in position 21 is Asp, Glu, Cys or Gly,
Xaa in position 22 is Gly or none, and
n=0, 1, 2 or 3;

$Xaa_1$ $Xaa_2$ $Xaa_3$ Pro Ile Pro $Xaa_7$ $Xaa_8$ $Xaa_9$ $Xaa_{10}$ $Xaa_{11}$ $Xaa_{12}$ $[Gly]$, $Xaa_{13}$ $Xaa_{14}$ $Xaa_{15}$ $Xaa_{16}$ $Xaa_{12}$ $Xaa_{18}$ $Xaa_{19}$ $Xaa_{20}$ $Xaa_{21}$ $Xaa_{22}$ $Xaa_{23}$ $Xaa_{24}$ (SEQ ID NO: 9);

wherein Xaa in position 1 is Asn, Ser, Gly, His, Ala, Pro, Arg or none,
Xaa in position 2 is Asn, Ala or Lys,
Xaa in position 3 is Pro, Gln, Gly, Ile or Leu,
Xaa in position 7 is Val or Ala,
Xaa in position 8 is Gly or Lys,
Xaa in position 9 is Glu, Asp, Lys, Phe or Thr,
Xaa in position 10 is Ile, Met, Val or Leu,
Xaa in position 11 is Tyr, Leu or none,
Xaa in position 12 is Ser or none,
Xaa in position 13 is Arg or none,
Xaa in position 14 is Asp, Arg, Trp, Ala or none,
Xaa in position 15 is Ile or none,
Xaa in position 16 is Tyr or none,
Xaa in position 17 is Lys or Arg,
Xaa in position 18 is Arg, Lys or Asp,
Xaa in position 19 is Trp or Gly,
Xaa in position 20 is Ile, Met, Val, Gln or Ala,
Xaa in position 21 is Ile, Val or Ala,
Xaa in position 22 is Leu, Met or Val,
Xaa in position 23 is Gly or Cys,
Xaa in position 24 is Leu or none,
n=1, 2 or 3; and $Xaa_1$ $Xaa_2$ Ile Ile $Xaa_5$ $Xaa_6$ $Xaa_7$ $Xaa_8$ $Xaa_9$ Leu $Xaa_{11}$ $[Gly]_n$ $[Arg]_n$ $Xaa_{12}$ $Xaa_{13}$ $Xaa_{14}$ $Xaa_{15}$ $Xaa_{16}$ $Xaa_{12}$ $Xaa_{18}$ $Xaa_{19}$ $Xaa_{20}$ $Xaa_{21}$ $Xaa_{22}$ $Xaa_{23}$ $Xaa_{24}$ $Xaa_{25}$ (SEQ ID NO: 15);

wherein Xaa in position 1 is Pro, Lys, Arg or none,
Xaa in position 2 is Glu, Arg, Phe or Lys,
Xaa in position 5 is Pro or Thr,
Xaa in position 6 is Met, Thr or Nleu,
Xaa in position 7 is Phe or Leu,
Xaa in position 8 is Ser, Thr, Ala or Met,
Xaa in position 9 is Ala, Glu or Leu,
Xaa in position 11 is Ser or none,
Xaa in position 12 is Ala, Arg or none,
Xaa in position 13 is Ile, Leu or none,
Xaa in position 14 is Ser, Ala, Leu or none,
Xaa in position 15 is Tyr, Glu or Asp, Xaa in position 16 is Gly or Asp,
Xaa in position 17 is Ala or Leu,
Xaa in position 18 is Thr, Ile, Val, Leu or Asn,
Xaa in position 19 is Pro, Thr or Ser,
Xaa in position 20 is Tyr, Phe, Nleu, His or Gln,
Xaa in position 21 is Asp, Asn, Leu or Ala,
Xaa in position 22 is Leu, Ile, Val or Asn,
Xaa in position 23 is Asn, Tyr, Cys or Gly,
Xaa in position 24 is Thr, Met, Ile, Ala, Val or none,
Xaa in position 25 is Gly or none,
n=1, 2 or 3 and m=0, 1, 2 or 3 independent of each other; wherein the terminal ends of each HIV specific peptide may be free carboxyl- or amino-groups, amides, acyls or acetyls; and wherein each peptide optionally is in the form of an acetate salt; over a period of 1-12 weeks; and b) a subsequent viral reactivation phase consisting of the administering of an effective amount of a reservoir purging agent.

In a further aspect the present invention relates to an effective amount of one or more HIV-specific peptide selected from the list consisting of the amino acid sequence shown in SEQ ID NO: 18 (Vacc-10), SEQ ID NO: 11 (Vacc-11), SEQ ID NO: 6 (Vacc-12) for use in method for reducing and/or delaying pathological effects of human immunodeficiency virus I (HIV) or for reducing the risk of developing acquired immunodeficiency syndrome (AIDS) in a human infected with HIV, the method comprising the steps of:

a) a therapeutic HIV-1 immunization phase consisting of the administering in one or more doses of said one or more HIV-specific peptide over a period of 1-12 weeks; and b) a subsequent viral reactivation phase consisting of the administering of an effective amount of a reservoir purging agent.

In some embodiments the one or more HIV-specific peptide is selected from the group of amino acid sequences of SEQ ID NOs: 1, 4, 9 and 15; wherein the terminal ends of each HIV specific peptide may be free carboxyl- or amino-groups, amides, acyls or acetyls; and wherein each peptide is in the form of an acetate salt.

In some embodiments the peptide consisting of the amino acid sequence shown in SEQ ID NO: 18 (Vacc-10) is in the form of an acetate salt.

In some embodiments the peptide consisting of the amino acid sequence shown in SEQ ID NO: 11 (Vacc-11) is in the form of an acetate salt.

In some embodiments the peptide consisting of the amino acid sequence shown in SEQ ID NO: 6 (Vacc-12) is in the form of an acetate salt.

In some embodiments the peptide consisting of the amino acid sequence shown in SEQ ID NO: 3 (Vacc-13) is in the form of an acetate salt.

In some embodiments one, two, three or four peptide acetate salts is/are used in the methods according to the invention.

DETAILED DISCLOSURE OF THE INVENTION

The present invention is based on the finding that the therapeutic use of a potent reservoir purging agent, such as a histone deacetylase (HDAC) inhibitor, will lead to short-term increases in HIV-1 transcription and long-term reductions in the HIV-1 reservoir size due to increased levels and responsiveness of HIV-1-specific cytotoxic T lymphocytes in Vacc-4x immunized subjects.

Definitions

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

"HIV" unless otherwise indicated generally denotes human immunodeficiency virus I.

"HIV disease" is composed of several stages including the acute HIV infection which often manifests itself as a flu-like infection and the early and medium stage symptomatic disease, which has several non-characteristic symptoms such as skin rashes, fatigue, night sweats, slight weight loss, mouth ulcers, and fungal skin and nail infections. Most HIV infected will experience mild symptoms such as these before developing more serious illnesses. It is generally believed that it takes five to seven years for the first mild symptoms to appear. As HIV disease progresses, some individuals may become quite ill even if they have not yet been diagnosed with AIDS (see below), the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition which progressively reduces the effectiveness of the immune system and leaves individuals susceptible to opportunistic infections and tumors.

"Reducing and/or delaying pathological effect of HIV" is in the present context meant to denote that use of the methods of the invention provides for a statistically significant reduction and/or delay in morbidity seen in individual infected with HIV which are treated according to the present invention. That is, the time of onset of manifest disease symptoms characterizing AIDS is later compared to non-treated controls and/or the number of pathological manifestations is reduced to controls not receiving the treatment of the present invention.

The term "peptide" is in the present context intended to mean both short peptides of from 2 to 10 amino acid residues, oligopeptides of from 11 to 100 amino acid residues, and polypeptides of more than 100 amino acid residues. When referring to amino acids in peptides, it is intended that the amino acids are L-amino acids, unless other information is provided.

A "variant" or "analogue" of a peptide refers to a peptide having an amino acid sequence that is substantially identical to a reference peptide, typically a native or "parent" polypeptide. The peptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having an the side chain —$(CH_2)_n NH_3$, where n is different from 4, and arginine may be substituted with an amino acid having the side chain —$(CH_2)_n NFC(=NH_2)NH_2$, where n is different from 3, etc. Similarly, the acidic amino acids aspartic acid and glutamic acid may be substituted with amino acid residues having the side chains —$(CH_2)_n COOH$, where n>2.

A "retro form" of a peptide is a form of a peptide where the order of the amino acids in N- to C-terminal direction has been inverted. For instance, the retro form of ALDFR is the peptide RFDLA.

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms, or when deducing the is the computer program BLAST, especially blastp, using default parameters. See, e.g., Altschul et al., 3. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%-99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term antigen denotes a substance of matter which is recognized by the immune system's specifically recognizing components (antibodies, T-cells).

The term "immunogen" is in the present context intended to denote a substance of matter, which is capable of inducing an adaptive immune response in an individual, where said adaptive immune response targets the immunogen. In other words, an immunogen is an antigen, which is capable of inducing immunity.

The terms "epitope", "antigenic determinant" and "antigenic site" are used interchangeably herein and denotes the region in an antigen or immunogen which is recognized by antibodies (in the case of antibody binding epitopes, also known as "B-cell epitopes") or by T-cell receptors when the epitope is complexed to an MHC molecule (in the case of T-cell receptor binding epitopes, i.e. "T-cell epitopes").

The term "immunogenically effective amount" has its usual meaning in the art, i.e. an amount of an immunogen, which is capable of inducing an immune response, which significantly engages pathogenic agents, which share immunological features with the immunogen.

The term "vaccine" is used for a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "T helper lymphocyte epitope" (a $T_H$ epitope) is peptide, which binds an MHC Class II molecule and can be presented on the surface of an antigen presenting cell (APC) bound to the MHC Class II molecule. An "immunological carrier" is generally a substance of matter which includes one or many $T_H$ epitopes, and which increase the immune response against an antigen to which it is coupled by ensuring that T-helper lymphocytes are activated and proliferate. Examples of known immunological carriers are the tetanus and diphtheria toxoids and keyhole limpet hemocyanin (KLH).

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

Specific Aspects and Embodiments of the Invention

One aspect of the present invention relates to the use of one or more HIV-specific peptide as defined above.

In certain embodiments, peptides comprise an N- or C-terminal modification, such as an amidation, acylation, or acetylation. When the C-terminal end of a peptide is an amide, suitable amides included those having the formula —C(O)—NR$^x$R$^y$, wherein R$^x$ and R$^y$ are independently selected from hydrogen and C$_{1-6}$ alkyl, which alkyl group may be substituted with one of more fluoro atoms, for example —CH$_3$, —CH$_2$CH$_3$ and —CF$_3$, a particular amide group which may be mentioned is —C(O)NH$_2$. When the N-terminal end of the peptide is acetylated, suitable acetylated N-terminal ends include those of formula —NH—C(O)R$^z$, wherein R$^z$ is hydrogen, C$_{1-6}$ alkyl, which alkyl group may be substituted with one of more fluoro atoms, for example —CH$_3$, —CH$_2$CH$_3$ and —CF$_3$, or phenyl.

Since the peptides are contemplated as vaccine agents, they are in certain embodiments coupled to a carrier molecule, such as an immunogenic carrier. The peptides may thus be linked to other molecules either as recombinant fusions (e.g. via CLIP technology) or through chemical linkages in an oriented (e.g. using heterobifunctional crosslinkers) or nonoriented fashion. Linking to carrier molecules such as for example diphtheria toxin, polylysine constructs etc, are all possible according to the invention.

The immunogenic carrier is conveniently selected from carrier proteins such as those conventionally used in the art (e.g. diphtheria or tetanus toxoid, KLH etc.), but it is also possible to use shorter peptides (T-helper epitopes) which can induce T-cell immunity in larger proportions of a population. Details about such T-helper epitopes can e.g. be found in WO 00/20027, which is hereby incorporated by reference herein—all immunologic carriers and "promiscuous" (i.e. universal) T-helper epitopes discussed therein are useful as immunogenic carriers in the present invention.

In certain embodiments, the carrier is a virus like particle, i.e. a particle sharing properties with virions without being infectious. Such virus-like particles may be provided chemically (e.g. Jennings and Bachmann Ann. Rev. Pharmacol. Toxicol. 2009. 49:303-26 Immunodrugs: Therapeutic VLP-based vaccines for chronic diseases) or using cloning techniques to generate fusion proteins (e.g. Peabody et al. J. Mol. Biol. 2008; 380: 252-63. Immunogenic display of diverse peptides on virus-like particles of RNA phage MS2). Another example is "Remune", an HIV vaccine originally made by Immune Response Corporation, which consists of formalin inactivated HIV that has been irradiated to destroy the viral genome. The company was started by Jonas Salk who used the same technique to generate the killed polio vaccine in widespread use today.

One aspect of the present invention relates to the use of an immunogenic composition (such as a vaccine composition) comprising a composition of at least one HIV-specific peptides, in combination with an effective amount of a reservoir purging agent, optionally together with a pharmaceutically acceptable diluent or vehicle and optionally one or more immunological adjuvant.

In common for aspects of the invention is that they all include embodiments where the at least one HIV-specific peptide is selected from the group of amino acid sequences of SEQ ID NOs: 1, 4, 9 and 15, as defined above; wherein the terminal ends of each HIV specific peptide may be free carboxyl- or amino-groups, amides, acyls or acetyls; and in the form of an acetate salt.

In some embodiments two or more of the Cys residues of said HIV-specific peptide may form part of an intrachain- or interchain disulphide binding, a —S—(CH$_2$)$_p$—S—, or a —(CH$_2$)$_p$— bridge wherein p=1-8 optionally intervened by one or more heteroatoms such as O, N and S and/or the said peptide sequences are immobilized to a solid support.

In some embodiments the amino acid sequence of SEQ ID NO: 1 is selected from the group of SEQ ID NO: 2 and SEQ ID NO: 3.

In some embodiments the amino acid sequence of SEQ ID NO: 4 is selected from the group of SEQ ID NO: 5, SEQ ID NO: 6, SEQ ID NO: 7 and SEQ ID NO: 8.

In some embodiments the amino acid sequence of SEQ ID NO: 9 is selected from the group of SEQ ID NO: 10, SEQ ID NO: 11, SEQ ID NO: 12, SEQ ID NO: 13 and SEQ ID NO: 14.

In some embodiments the amino acid sequence of SEQ ID NO: 15 is selected from the group of SEQ ID NO: 16, SEQ ID NO: 17, SEQ ID NO: 18, SEQ ID NO: 19 and SEQ ID NO: 20.

In some embodiments the at least one HIV-specific peptide comprises at least, two, three, or four peptides selected from each of the groups of SEQ ID NO: 1, SEQ ID NO: 4, SEQ ID NO: 9 and SEQ ID NO: 15.

In some embodiments the at least one HIV-specific peptide consists of or comprises the peptides of SEQ ID NO: 3, SEQ ID NO: 6, SEQ ID NO: 11 and SEQ ID NO: 18.

Preparation of immunogenic compositions includes the use of state-of-the-art constituents such as immunological adjuvants. Apart from these adjuvants, which are detailed, by way of example, below, immunogenic compositions are prepared as generally taught in the art:

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, nasal, buccal, sublingual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10% (w/w), preferably 1-2% (w/w). Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and may contain 10-95% (w/w) of active ingredient, preferably 25-70% (w/w).

The peptides may be formulated into a vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and organic bases such as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of immunity desired. Suitable dosage ranges are of the order of several hundred micrograms of active ingredient per vaccination with a preferred range from about 0.1 µg to 2,000 µg (even though higher amounts in the 1-10 mg range are contemplated), such as in the range from about 0.5 µg to 1,800 µg, preferably in the range from 1 µg to 1,500 µg and especially in the range from about 100 µg to 1200 µg. Suitable regimens for initial administration and booster shots are also variable but are typified by an initial administration followed by subsequent inoculations or other administrations.

Some of the peptides are sufficiently immunogenic in a vaccine, but for some of the others the immune response will be enhanced if the vaccine further comprises an adjuvant substance. The immunogenic molecules described herein can therefore be formulated with adjuvants:

The adjuvants to be combined are known to induce humoral responses and include: i) Salt suspensions (e.g. varieties of salts containing aluminum ions or calcium ions), ii) Oil-in-water emulsions (e.g. varieties of squalane-based or squalene-based emulsions), iii) Water-in-oil emulsions (e.g. Montanide ISA51 or ISA720), iv) Neutral liposomes, v) Cationic liposomes, vi) Microspheres, vii) Immunostimulating complexes (e.g. ISCOMs or ISCOMATRIX), viii) Pattern-recognition receptor agonists (e.g. agonists for C-type lectin receptors (CLRs), NOD-like receptors (NLRs), RIG-like helicases (RLHs), Triggering receptor expressed on myeloid cells (TREMs) and Toll-like receptors (TLRs)), ix) Saponins (i.e. Any saponin derived from *Quillaja saponaria* or *Platycodon grandiflorum*), x) Virosomes/Virus-like particles, xi) Enterotoxins (i.e. Cholera toxin, CTA1-DD or *Escherichia coli* heat-labile enterotoxin), and combinations thereof.

For a further enhancement of the vaccine antigenic properties, they could be combined with a well-known adjuvant with an oral immune modulant or adjuvant such as a Cox-2 inhibitor or a immunomodulating compound.

A further aspect of the invention is the use of the vaccine combined with adjuvant, with one or more further therapeutic agents, such as an (oral) immunomodulating agent and/or a second reservoir purging agent.

The terms "therapeutic agent", such as "immunomodulating agent" or virus reservoir purging agent as used herein, includes but is not limited to cytokines, such as interferons, monoclonal antibodies, such as anti-PD1 antibodies and other checkpoint inhibitors, cyclophosphamide, Thalidomide, Levamisole, and Lenalidomide.

"A virus reservoir purging agent", includes but is not limited to auranofin, IL-7, prostratin, bryostatin, HDAC inhibitors, such as vorinostat, Disulfiram and any suitable agent disclosed in any one of WO2013050422, WO2012051492 A3 and in Barton et al., Clinical Pharmacology & Therapeutics (2013); 93 1, 46-561, including but not limited to a NF-kappa-B-inducer selected from the group comprising: PMA, prostratin, bryostatin and TNF-alpha, and/or b) a histone deacetylase inhibitor selected from the different families (hydroxamates, cyclic peptides, aliphatic acids, and benzamides) including: TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103. Any of the above virus reservoir purging agents may be used alone or in combination with any one other suitable virus reservoir purging agent, such as with another class of HIV inducers.

DNA methylation, probably together with repressive histone modifications, may also contribute to a "lock" in a silent state of the provirus and makes its return to an active state difficult. These observations suggest that HDAC or HMT or DNA methylation inhibitors together with efficient cART constitute good anti-latency drug candidates aimed at reducing/eliminating the pool of latent reservoirs to a level bearable by the host immune system.

Accordingly suitable immunomodulatory compounds or purging agents may be DNA methylation inhibitors selected from the two classes (non-nucleoside and nucleoside demethylating agents) including: 5-azacytidine (azacitidine), Sinefungin, 5-aza-2'-deoxycytidine (5-aza-CdR, decitabine), 1-3-Darabinofuranosyl-5-azacytosine (fazarabine) and dihydro-5-azacytidine (DHAC), 5-fluorodeoxycytidine (FdC), oligodeoxynucleotide duplexes containing 2-H pyrimidinone, zebularine, antisense oligodeoxynucleotides (ODNs), MG98, (−)-epigallocatechin-3-gallate, hydralazine, procaine and procainamide.

Other suitable immunomodulatory compounds or purging agents to be used according to the present invention includes histone deacetylase inhibitor selected from the different families of HDACI (hydroxamates, cyclic peptides, aliphatic acids, and benzamides) including TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103.

Other suitable immunomodulatory compounds or purging agents to be used according to the present invention includes histone methyltransferase inhibitors (chaetocin and BIX-01294); Inhibitors of Enhances of Zeste 2 (EZH2)—such as 3-deazaneplanocin A (DZNep) used alone or in combination with other classes of immunomodulatory compounds or purging agents.

Other suitable adjuvants include response-selective C5a agonists, such as EP54 and EP67 described in Hung C Y et al. An agonist of human complement fragment C5a enhances vaccine immunity against *Coccidioides* infection. Vaccine (2012) and Kollessery G et al. Tumor-specific peptide based vaccines containing the conformationally biased, response-selective C5a agonists EP54 and EP67 protect against aggressive large B cell lymphoma in a syngeneic murine model. Vaccine (2011) 29: 5904-10.

Various methods of achieving adjuvant effect for the vaccine are thus known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein, but a number of later publications also deal with the technology of incorporating adjuvants: Roestenberg M et al., PLoS One. 2008; 3(12):e3960. Epub 2008 Dec. 18; Relyveld E and Chermann J C, Biomed Pharmacother. 1994; 48(2):79-83; Hsu F J et al., Blood. 1997 May 1; 89(9):3129-35; Galli G et al., Proc Natl Acad Sci USA. 2009 May 12; 106(19):7962-7. Epub 2009 Apr. 27; Bojang K A et al., Lancet. 2001 Dec. 8; 358(9297):1927-34; Odunsi K et al., Proc Natl Acad Sci USA. 2007 Jul. 31; 104(31):12837-42. Epub 2007 Jul. 25; Patel G B and Sprott G D; Crit Rev Biotechnol. 1999; 19(4):317-57. Review; Agger E M et al., PLoS One. 2008 Sep. 8; 3(9):e3116; Kirby D J et al. J Drug Target. 2008 May; 16(4): 282-93; Florindo H F et al., Vaccine. 2008 Aug. 5; 26(33):4168-77. Epub 2008 Jun. 17; Sun H X et al., Vaccine. 2009 May 28; Guy B, Nat Rev Microbiol. 2007 July; 5(7):505-17. Review; Vandepapelière P et al., Vaccine. 2008 Mar. 4; 26(10):1375-86. Epub 2008 Jan. 14; Ghochikyan A et al. Vaccine. 2006 Mar. 20; 24(13): 2275-82. Epub 2005 Dec. 5; Xie Y et al., Vaccine. 2008 Jun. 25; 26(27-28):3452-60. Epub 2008 May 1; Chung Y C et al., Vaccine. 2008 Mar. 28; 26(15):1855-62. Epub 2008 Feb. 25; Maier M et al., Vaccine. 2005 Oct. 25; 23(44): 5149-59; Sundling C et al., J Gen Virol. 2008 December; 89(Pt 12):2954-64.

In the methods and compositions of the invention the at least one HIV-specific peptide and the reservoir purging agent, may be administered in combination with one or more further therapeutically active agents, such as agents for the treatment and or prevention of HIV and/or AIDS.

The terms "therapeutic active agent", such as "immunomodulating agent" or virus reservoir purging agent as used herein, includes but is not limited to cytokines, such as interferons, monoclonal antibodies, such as ant-PD1 antibodies, cyclophosphamide, Thalidomide, Levamisole, and Lenalidomide.

"A virus reservoir purging agent", includes but is not limited to auranofin, IL-7, prostratin, bryostatin, HDAC inhibitors, such as vorinostat, and Disulfiram, and the further agents described herein.

The failure of antiretroviral therapy (ART) to eradicate HIV-1 infection lies in the observation that HIV-1 remains quiescent in latent reservoirs. Latently infected resting CD4+ cells (either naive or long lived memory cells) carry transcriptionally silent HIV-1 and represent the predominant reservoir of HIV-1 infection. Other cells may also act as reservoirs (Reviewed in Alexaki et al., 2008, Curr. HIV Res. 6:388-400), such as macrophages, dendritic cells and astrocytes (where HIV-1 infection occurs via a CD4-independent mechanism). It is these latent reservoirs that represent the major challenge to eradication of HIV-1 infection. Approaches towards eradication include attempts to purge reservoirs by selective activation of latently infected cells (such as memory cells) in the presence of ART such that released virus may not infect and replicate in neighbouring cells (Richman et al., 2009, Science 323:1304-1307). Agents include histone deacetylase inhibitors, cytokines, such as IL-2 and IL-7, as well as bryostatin, the protein kinase C activator (Kovochich et al., 2011, PLoS ONE 6 (4):e18270). Therapeutic vaccines have the advantage of being able to penetrate sanctuary sites less well accessed by ART such as lymphoid tissue (Panteleo et al., 1991, Proc. Natl. Acad. Sci. USA 88:9838-42; Fox et al., 1991, J. Infect. Dis. 164:1051-57) and the central nervous system (Alexaki et al., 2008, Curr. HIV Res. 6:388-400), that represent regions for viral persistence. This relates to therapeutic interventions targeting both the virus itself as well as HIV-associated immune activation.

A number of studies have been conducted with the aim of providing compounds that can safely and effectively be used to treat diseases associated with abnormal production of TNF-α. See, e.g., Marriott, J. B., et al, Expert Opin. Biol. Ther. (4): 1-8 (2001); G. W. Muller, et al, Journal of Medicinal Chemistry, 39(17): 3238-3240 (1996); and G. W. Muller, et al, Bioorganic & Medicinal Chemistry Letters, 8: 2669-2674 (1998). Some studies have focused on a group of compounds selected for their capacity to potently inhibit TNF-α production by LPS stimulated PBMC. L. G. Corral, et al, Ann. Rheum. Dis., 58 (suppl I): 1107-1113 (1999). These compounds, often referred to as immunomodulatory compounds, show not only potent inhibition of TNF-α, but also marked inhibition of LPS induced monocyte IL1B and IL12 production. LPS induced IL6 is also inhibited by immunomodulatory compounds, albeit partially. These compounds are potent stimulators of LPS induced IL10. Particular examples include, but are not limited to, the substituted 2-(2,6-dioxopiperidin-3-yl)phthalimides and substituted 2-(2,6-dioxopiperidin-3-yl)-1-oxoisoindoles as described in U.S. Pat. Nos. 6,281,230 and 6,316,471. Monocyte/macrophage function is part of the Innate Immune System that serves as a first line of defense against an infection. By modulating the host's monocytes and macrophages, immunomodulatory compounds can change the dynamics of the response to a viral infection, such as influenza.

Histone deacetylases (HDAC) are a class of enzymes that remove acetyl groups from N-acetylated lysines amino acid on histone proteins. Currently 18 HDACs have been identified in mammals. They have been divided into four classes based on cellular localization, function, and sequence similarity. Class I includes HDACs 1, 2, 3, and 8 which are found primarily in the nucleus. Class II HDACs (HDACs 4, 5, 6, 7 9, and 10) are found primarily in the cytoplasm but may be able to shuttle between the nucleus and the cytoplasm; class IIa comprises four HDACs (HDACs 4, 5, 7 and 9) while class IIb comprises two HDACs (HDACs 6 and 10) which are expressed only in the cytoplasm. HDAC11, which is ubiquitously expressed, shares sequence similarities with both class I and class II HDACs and represents Class IV. Class III (also called "sirtuin family") groups NAD+-dependent proteins which do not act primarily on histones.

In the methods of the invention the at least one HIV-specific peptide, is administered in a specific dosage regimen together with a reservoir purging agent, and optionally together with another immunomodulatory compound and/or a second reservoir purging agent, such as another histone deacetylase (HDAC) inhibitor.

The immunomodulatory compounds may be selected from anti-PD1 antibodies, such as MDX-1106 (Merck), THALOMID® (thalidomide), anti-PD1 antibodies, cyclophosphamide, Levamisole, lenalidomide, CC-4047 (pomalidomide), CC-11006 (Celgene), and CC-10015 (Celgene), and immunomodulatory compound described in any one of WO2007028047, WO2002059106, and WO2002094180. The immunomodulatory compound may be selected from 4-(amino)-2-(2,6-dioxo(3-piperidyl))-isoindoline-1,3-dione and 3-(4-amino-1-oxo-1,3-dihydro-isoindol-2-yl)-piperidine-2,6-dione. In particular the immunomodulatory compound is lenalidomide. The immunomodulatory compound may be enantiomerically pure. The second reservoir purging agent, such as a histone deacetylase (HDAC) inhibitor, may be selected from M344 (4-(dimethylamino)-N-[7-(hydroxyamino)-7-oxoheptyl] benzamide), chidamide (C5055/HBI-800), 4SC-202, (4SC), Resminostat (4SC), hydroxamic acids such as vorinostat (SAHA), belinostat (PXD101), LAQ824, trichostatin A and panobinostat (LBH589); benzamides such as entinostat (MS-275), CI994, and mocetinostat (MGCD0103), cyclic tetrapeptides (such as trapoxin, such as trapoxin B), and the depsipeptides, such as romidepsin (Istodax® (Celgene)), electrophilic ketones, and the aliphatic acid compounds such as phenylbutyrate, valproic acid, Oxamflatin, ITF2357 (generic givinostat), Apicidin, MC1293, CG05, and CG06; compounds that activate transcription factors including NF-KappaB, Prostratin, auranofin, bryostatin, a nontumorigenic phorbol ester, DPP (12-deoxyphorbol-13-phenylacetate), PMA, and Phorbol 12-myristate 13-acetate (PMA); Compounds that activate HIV mRNA elongation including P-TEF-b kinase and hexamethylbisacetamide (HMBA); IL-7; T-cell stimulating factors including anti-CD3/CD28-T-cell stimulating Ab's; Kinase inhibitors including Tyrphostin A, Tyrphostin B, and Tyrphostin C; PTEN (phosphatase and tensin homologue) gene inhibitors including SF1670 (Echelon Bioscience), Disulfiram (DSF), an inhibitor of acetaldehyde dehydrogenase, Protein Tyrosine Phosphatase Inhibitors including bpV(HOpic), bpV(phen), and bpV(pic) (Calbiochem; EMD Millipore), Toll-like receptors agonists including Toll-like receptor-9 (TLR9) and Toll-like receptor-7 (TLR9) agonists, quercetin, lipoic acid, sodium butyrate, TNF-alpha, PHA, Tat.

In the methods of the invention the components of the at least one HIV-specific peptide and/or the one or more further therapeutically active agents, may be administered simultaneously, sequentially or separately in any order.

Thus the invention provides a pharmaceutical composition comprising one, two or more components of the at least one HIV-specific peptide and/or the one or more further therapeutically active agents optionally in combination with one or more pharmaceutically acceptable adjuvants, diluents or carriers.

Similarly, the invention also provides a combination product comprising of components of the at least one HIV-specific peptide and/or the one or more further therapeutically active agents, wherein each of component is formulated in admixture with a pharmaceutically-acceptable adjuvant, diluent or carrier. In this aspect of the invention, the combination product may be either a single (combination) pharmaceutical formulation or a kit-of-parts. In a kit-of-parts some or all of the components may be formulated separately and may each be provided in a form that is suitable for administration in conjunction with the other(s).

The component(s) may also be provided for use, e.g. with instructions for use, in combination with one or more further component(s) as defined above.

The peptides for use in the invention may be produced synthetically using art recognised methods. Further details for the synthetic production of such peptides are found in the Examples. Alternatively the peptides may be produced recombinantly. When recombinantly producing the peptides for use in the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment of the invention. Preferably, this stable cell line secretes or carries the peptide expression product, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, E. coli is typically transformed using pBR322, a plasmid derived from an E. coli species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in recombinant DNA construction include the β-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published.

In addition to prokaryotes, eukaryotic microbes, such as yeast cultures may also be used, and also here the promoter should be capable of driving expression. *Saccharomyces cerevisiase*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980).

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also incorporated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. Examples of such useful host cell lines are VERO and HeLa cells, Chinese hamster ovary (CHO) cell lines, and W138, Per.C6, BHK, COS-7 293, *Spodoptera frugiperda* (SF) cells, *Drosophila melanogaster* cell lines (such as Schneider 2 ($S_2$)), and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., other Polyoma viruses, Adeno, VSV, BPV) or may be provided by the host cell chromosomal replication mechanism. If the vector is integrated into the host cell chromosome, the latter is often sufficient.

As for routes of administration and administration schemes of polypeptide based vaccines which have been detailed above, these are also applicable for the nucleic acid vaccines of the invention and all discussions above pertaining to routes of administration and administration schemes for polypeptides apply mutatis mutandis to nucleic acids. To this should be added that nucleic acid vaccines can also be administered intravenously and intraarterially. Furthermore, it is well-known in the art that nucleic acid vaccines can be administered by use of a so-called gene gun and/or by use of electroporation, and hence also these and equivalent modes of administration are regarded as part of the present invention.

Under normal circumstances, the nucleic acid fragment is introduced in the form of a vector wherein expression is under control of a viral promoter. For more detailed discussions of vectors according to the invention, cf. the discussion above. Also, detailed disclosures relating to the formulation and use of nucleic acid vaccines are available, cf. Donnelly 33 et al, 1997, Annu. Rev. Immunol. 15: 617-648 and Donnelly 33 et al., 1997, Life Sciences 60: 163-172. Both of these references are incorporated by reference herein.

An alternative of using peptide immunogens or nucleic acid immunogens is the use of live immunogen technology. This entails administering a non-pathogenic microorganism which has been transformed with a nucleic acid fragment or a vector of the present invention. The non-pathogenic microorganism can be any suitable attenuated bacterial strain (attenuated by means of passaging or by means of removal of pathogenic expression products by recombinant DNA technology), e.g. *Mycobacterium bovis* BCG, non-pathogenic *Streptococcus* spp., *E. coli*, *Salmonella* spp., *Vibrio cholerae*, *Shigella*, etc. Reviews dealing with preparation of state-of-the-art live vaccines can e.g. be found in Saliou P, 1995, Rev. Prat. 45: 1492-1496 and Walker P D, 1992, Vaccine 10: 977-990, both incorporated by reference herein. For details about the nucleic acid fragments and vectors used in such live vaccines, cf. the discussion below.

As an alternative to bacterial live immunogens, the nucleic acid fragment of the invention can be incorporated in a non-virulent viral vaccine vector such as a vaccinia strain or any other suitable poxvirus.

Normally, the non-pathogenic microorganism or virus is administered only once to a subject, but in certain cases it may be necessary to administer the microorganism/virus more than once in a lifetime in order to maintain protective immunity. It is even contemplated that immunization schemes as those detailed above for polypeptide vaccination will be useful when using live or virus vaccines.

Alternatively, live or virus immunization is combined with previous or subsequent polypeptide and/or nucleic acid immunization. For instance, it is possible to effect primary immunization with a live or virus vaccine followed by subsequent booster immunizations using the polypeptide or nucleic acid approach.

PREAMBLE TO EXAMPLES

HIV-Specific Peptides for Use According to the Invention

The present invention involves the use of HIV-specific peptides based on conserved regions of HIV gag p24, antigens in free or carrier-bound form comprising at least one of the said peptides.

The HIV-specific peptides for use according to the invention originate from the four different conserved areas of the HIV-1 core protein p24, having the properties of maintaining the uniqueness (sensitivity and specificity) of the HIV-1-epitope. Further these peptides possess no recognized cytotoxic T lymphocyte (CTL) antagonistic effect and have at least one potential CTL epitope.

The HIV-specific peptides, for use according to the invention, which have met the above criteria are selected from the group of amino acid sequences of SEQ ID NOs: 1, 4, 9 and 15, as defined above; wherein the terminal ends of each HIV specific peptide may be free carboxyl- or amino-groups, amides, acyls or acetyls; or acetate salts of any of the HIV specific peptides.

The HIV-specific peptide sequences have the potential to serve as a particularly good antigen wherein the antigen comprises at least one peptide selected from the group of sequences of SEQ ID NO: 1, SEQ ID NO: 4, SEQ ID NO:

9 or SEQ ID NO: 15. The antigenicity may be adapted through adjusting the ratio or concentration of different peptides or size of the peptides by for instance dimerisation or polymerisation and/or immobilisation to a solid phase. The antigen may comprise two or more polypeptide sequences which are either linked by a bridge for instance a disulphide bridge between the Cys residues of the chains or bridges like $C_1$-$C_8$ alkylene possibly intervened by one or more heteroatoms like O, S, or N or preferably they are unlinked. The chains may be immobilized to a solid phase in monomeric, dimeric or oligomeric forms. Further amino acids may be added to the ends in order to achieve an arm to facilitate immobilization.

All amino acids in the HIV-specific peptides of the invention can be in both D- or L-form, although the naturally occurring L-form is preferred.

The C- and N-terminal ends of the HIV-specific peptide sequences could deviate from the natural sequences by modification of the terminal $NH_2$-group and/or COOH-group, they may for instance be acylated, acetylated, amidated or salts thereof; or modified to provide a binding site for a carrier or another molecule. When the C-terminal end of a peptide is an amide, suitable amides included those having the formula —C(O)—$NR^xR^y$, wherein $R^x$ and $R^y$ are independently selected from hydrogen and $C_{1-6}$ alkyl, which alkyl group may be substituted with one of more fluoro atoms, for example —$CH_3$, —$CH_2CH_3$ and —$CF_3$, a particular amide group which may be mentioned is —C(O)$NH_2$. When the N-terminal end of the peptide is acetylated, suitable acetylated N-terminal ends include those of formula —NH—C(O)$R^z$, wherein $R^z$ is hydrogen, $C_{1-6}$ alkyl, which alkyl group may be substituted with one of more fluoro atoms, for example —$CH_3$, —$CH_2CH_3$ and —$CF_3$, or phenyl.

The HIV-specific peptides for use according to the invention consist of 6 to 50 amino acids, preferably between 10 and 30 amino acids. They cover all natural variation of amino acids in the identified positions.

The polypeptide antigen for use according to the invention is either in a free or in a carrier-bound form. The carrier or solid phase to which the peptide is optionally bound can be selected from a wide variety of known carriers. It should be selected with regard to the intended use of the immobilized polypeptide as an immunizing component in a vaccine.

In a preferred embodiment the HIV specific peptides for use according to the present invention comprises antigens containing the peptides of the SEQ ID NOs: 1, 4, 9 and 15, more preferably the peptides occur in the ratio 1:1:1:1 w/w.

In a further preferred embodiment the HIV specific peptides for use according to the invention comprise the following:
  RALGPAATLQTPWTASLGVG (SEQ ID NO: 3)
  RWLLLGLNPLVGGGRLYSPTSILG (SEQ ID NO: 6)
  RAIPIPAGTLLSGGGRAIYKRTAILG (SEQ ID NO: 11) and
  RFIIPNIFTALSGGRRALLYGATPYAIG (SEQ ID NO: 18) (NI in position 6 is Norleucine) or salts thereof, particularly acetate salts.

In some embodiments the HIV specific peptides for use according to the invention are modified at the C-terminus as follows:
  RALGPAATLQTPWTASLGVG-$NH_2$ (SEQ ID NO: 3)
  RWLLLGLNPLVGGGRLYSPTSILG-$NH_2$ (SEQ ID NO: 6)
  RAIPIPAGTLLSGGGRAIYKRTAILG-$NH_2$ (SEQ ID NO: 11) and
  RFIIPNIFTALSGGRRALLYGATPYAIG-$NH_2$ (SEQ ID NO: 18)
    or salts thereof, particularly acetate salts. (In this application also referred to in the examples as Vacc-4x).

One of the sequences contains a B-cell epitope and will activate the humoral immune system, whereas the other sequences contribute with CTL-epitopes and the amino acid changes implemented within the frame of the CTL-epitope are designed to achieve enhanced binding. Other amino acid changes have been conducted in order to facilitate the synthesis of the peptide and/or increase the solubility of the peptide.

Description of the Preparation of the Peptides

The peptides of the invention can be produced by any known method of producing a linear amino acid sequence, such as recombinant DNA techniques. A nucleic acid sequence which encodes a peptide of the invention or a multimer of the said peptides, is introduced into an expression vector. Suitable expression vectors are for instance plasmids, cosmids, viruses and YAC (yeast artificial chromosome) which comprise necessary control regions for replication and expression. The expression vector may be stimulated to expression in a host cell. Suitable host cells are for example bacteria, yeast cells and mammal cells. Such techniques are well known in the art and described for instance by Sambrook et al., Molecular Cloning: A Laboratory Manual, Cold Spring Harbor Laboratory Press, Cold Spring Harbor, 1989. Other well-known techniques are degradation or synthesis by coupling of one amino acid residue to the next one in liquid phase or preferably on a solid phase (resin) for instance by the so-called Merrifield synthesis. See for instance Barany and Merrifield in the Peptides, Analysis, Synthesis, Biology, Vol. 2, E. Gross and Meinhofer, Ed. (Acad. Press, N.Y., 1980), Kneib-Coronier and Mullen Int. 3. Peptide Protein Res., 30, p. 705-739 (1987) and Fields and Noble Int. J. Peptide Protein Res., 35, p. 161-214 (1990).

In case a linked or cyclic peptide is desired, the amino acid sequence is subjected to a chemical oxidation step in order to cyclize or link the two cysteine residues within one or between two peptide sequences, when the appropriate linear amino acid sequences are synthesized, see Akaji et al., Tetrahedron Letter, 33, 8, p. 1073-1076, 1992.

General Description of Synthesis

The amino acid derivatives were supplied by Bachem AG, Switzerland.

The peptides described herein preferably have a free amino group at the N-terminus and an amidated C-terminus. The counter ion of all peptides described herein is acetate which is bound in ionic form to charged functional groups (i.e. guanidino side chains arginine and the ε-amino groups of lysine [Vacc-11] and the side chains of arginine [Vacc-10, Vacc-12 and Vacc-13]). All amino acid residues except the achiral glycine are in the L-configuration. The peptides described herein were assembled on tricyclic amide linker resins utilising an 9-fluorenylmethyloxycarbonyl (Fmoc) strategy.

In brief the tricyclic amide linker resin is transferred into a solid phase peptide synthesis (SPPS)-reactor with a stirrer. Synthesis is then started with a 9-fluorenylmethyloxycarbonyl (Fmoc)-deprotection of the resin according to the general description given below, followed by a coupling procedure with Fmoc-Gly-OH. This step is again followed by an Fmoc-deprotection and subsequent coupling of the amino acid derivates, peptides or dipeptides according to the sequence. The last coupling step is performed with side-chain protected Fmoc-Arg-OH. After final Fmoc-deprotection, the peptide resin is dried in a desiccator under reduced pressure.

Fmoc-Deprotecting Procedure:
Step 1: Washing;
Step 2: Fmoc-deprotection;
Steps 3-9: Washing.

Each step consists of addition of solvents/reagents, stirring at room temperature and filtration.

The peptide resin is treated with cold TFA in the presence of deionised water and 1, 2-Ethanedithiol (EDT), (Vacc-10 and Vacc-13) or triisopropylsilane (TIS) (Vacc-11 and Vacc-12) for approximately two to three hours at room temperature. After filtering off and washing the resin with TFA, the peptide is precipitated in diisopropyl ether (IPE). It is then filtered off, washed with IPE and dried in a desiccator under reduced pressure.

The material obtained in the previous stage is purified by preparative HPLC on reversed phase columns with acetonitrile (ACN) gradient elution and ultraviolet (UV) detection at A=220 nano-meters (nm) using a TEAP and/or TFA system. Vacc-10 is only purified using the TFA system.

For Vacc-13, a perchlorate system for preparative HPLC purification prior to using TEAP and TFA system has been introduced. Sodium perchlorate is listed as a raw material.

The last stage of manufacture of Vacc-4x acetate is the exchange from the TFA salt, obtained in stage three, into the acetate salt by ion exchange. The lyophilised material from one or several combined preparative HPLC runs is dissolved in varying concentrations of acetic acid or in purified water according to the properties of the individual peptides. The dissolved peptide is loaded onto the ion exchange resin (acetate form) and equilibrated with 5% acetic acid (or 20% purified water for Vacc-13). The elution is performed with 5% acetic acid (or purified water for Vacc-13), checked by thin-layer chromatography (TLC), filtered through a 0.2 µm membrane filter and lyophilised to yield the final product as a white to off-white powder.

Although the Vacc-4x formulation does not contain any ionic excipients, the peptides and their counter ions (acetate) account for a certain osmolality. The range of 10-100 mOsm/kg was defined based on the result obtained for the technical sample. Potential variability due to the four peptides is taken into account. For the drug product, approximately 1 mg of each of the four Vacc-4x peptides was used. The lyophilisate is reconstituted with 0.30 mL of WFI. Taking the acetic acid contents of the peptides listed in table 1 into account, the acetic acid content of Vacc-4x is approximately 0.40 mg in 0.30 mL of solution. The theoretical osmolality is approximately 23 mOsmol/L by calculation, which correlates well with the values determined in the Vacc-4x batches (20-23 mOsmol/kg).

TABLE 1

Acetic acid contents of the four peptides (GMP grade material, two batches each)

| Active substance | Peptide batch used for Vacc-4x batches 1011584 and 1012951 | Acetic acid content [%] | Peptide batch used for Vacc-4x batch 1018724 | Acetic acid content [%] |
| --- | --- | --- | --- | --- |
| Vacc-10 Acetate | 1008290 | 11.3 | 1015501 | 12.2 |
| Vacc-11 Acetate | 1009945 | 17.2 | 1015502 | 14.8 |
| Vacc-12 Acetate | 1008294 | 9.9 | 1015503 | 10.0 |
| Vacc-13 Acetate | 1008296 | 4.6 | 1015504 | 5.1 |

Example 1

Preparation of KALGPGATLQTPWTACQGVG-NH$_2$ (SEQ ID NO:2)

The peptide was synthesized in amide form, from corresponding starting materials according to the general description of synthesis. The purity was determined by HPLC analysis and the structure was confirmed by amino acid analysis and mass spectrometry (LDI-MS).

Preparation of RALGPAATLQTPWTASLGVG (SEQ ID NO:3)

The peptide was synthesized in amide form, from corresponding starting materials according to the general description of synthesis. The purity was determined by HPLC analysis and the structure was confirmed by amino acid analysis and mass spectrometry (LDI-MS).

Molecular formula: $C_{88}H_{144}O_{25}N_{26}$

Preparation of WIIPGLNPLVGGGKLYSPTSILCG-NH$_2$ (SEQ ID NO: 5)

The peptide was synthesized in amide form, from the corresponding starting materials according to the general description of synthesis. The purity was determined by HPLC analysis and the structure was confirmed by amino acid analysis and mass spectrometry (LDI-MS).

Mass spectral analysis: Theoretical molecular weight: 2454.9

Experimental molecular weight: 2454.8 ES+

Preparation of RWLLLGLNPLVGGGRLYSPTSILG (SEQ ID NO: 6)

The peptide was synthesized in amide form, from the corresponding starting materials according to the general description of synthesis. The purity was determined by HPLC analysis and the structure was confirmed by amino acid analysis and mass spectrometry (LDI-MS).

Molecular weight (free base): 2552
Molecular formula: $C_{119}H_{195}O_{29}N_{33}$ Preparation of KILLGLNPLVGGGRLYSPTSILG (SEQ ID NO: 7), RLLLGLNPLVGGGRLYSPTTILG (SEQ ID NO: 8) and NIPIPVGDIYGGGDIYKRWQALCL (SEQ ID NO: 21)

The peptides are synthesized in amide form, from the corresponding starting materials according to the general description of synthesis. The purity are determined by HPLC analysis and the structures are confirmed by amino acid analysis and mass spectrometry (LDI-MS).

Preparation of
RNIPIPVGDIYGGGDIYKRWQALCL (SEQ ID NO: 10)

The peptide was synthesized in amide form, from the corresponding starting materials according to the general description of synthesis. The purity was determined by HPLC analysis and the structure was confirmed by amino acid analysis and mass spectrometry (LDI-MS).
Mass spectral analysis: Theoretical molecular weight: 2817.3
Experimental molecular weight: 2813.7 ES+

Preparation of
RAIPIPAGTLLSGGGRAIYKRWAILG (SEQ ID NO: 11)

The peptide was synthesized in amide form, from the corresponding starting materials according to the general description of synthesis. The purity was determined by HPLC analysis and the structure was confirmed by amino acid analysis and mass spectrometry (LDI-MS).
Molecular weight (free base): 2707
Molecular formula: $C_{125}H_{208}O_{29}N_{38}$ Preparation of ALPIPAGFIYGGGRIYKRWQALG
(SEQ ID NO: 12),
KIPIPVGFIGGGWIYKRWAILG (SEQ ID NO: 13)
and KIPIPVGTLLSGGGRIYKRWAILG (SEQ ID NO: 14)

The peptides are synthesized in amide form, from the corresponding starting materials according to the general description of synthesis. The purity are determined by HPLC analysis and the structures are confirmed by amino acid analysis and mass spectrometry (LDI-MS).

Preparation of
KFIIPNIFSALGGAISYDLNTNILNCI (SEQ ID NO: 16)

The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).
Mass spectral analysis: Theoretical molecular weight: 2783.3
Experimental molecular weight: 2783.3 ES+

Preparation of
KFIIPNIFSALSGGGAISYDLNTFLNCIG (SEQ ID NO: 17)

The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).
Mass spectral analysis: Theoretical molecular weight: 2932.4

Experimental molecular weight: 2931.8 ES+

Preparation of
RFIIPNIFTALSGGRRALLYGATPYAIG (SEQ ID NO: 18)

The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).
Molecular weight (free base): 2894
Molecular formula: $C_{137}H_{217}O_{32}N_{37}$ Preparation of KIIPNIFSALGGGRLLYGATPYAIG
(SEQ ID NO: 19),
RIIPNIFTALSGGGRLLYGATPYAIG (SEQ ID NO: 20) and WIIPNIFSALGGAISYDLNTNILNCI
(SEQ ID NO: 22)

The peptides are synthesized in amide form, from the corresponding starting materials according to the general description of synthesis. The purity are determined by HPLC analysis and the structures are confirmed by amino acid analysis and mass spectrometry (LDI-MS).

Example 2

A vaccine comprising the peptides of the SEQ ID NOs: 3, 6, 11 and 18 was prepared (also referred to herein as Vacc-4x). The freeze-dried peptides were dissolved in sterile water at a final concentration of 4 mg/ml. The final salt concentration was 0.9%. A preparation of a granulocyte-macrophage-colony stimulating factor (GM-CSF) was also prepared, according to the manufacturer's directions for use, to a final concentration of 0.3 mg/ml. The two solutions are administered intracutaneously. A typical injection dose is 100 µl.

Example 3

An antigen solution or suspension is mixed with equal parts of Freund's adjuvant of Behring, complete or incomplete, and is then finely emulsified by being drawn up into, and vigorously pressed out of, an injection syringe, or with a homogenisator. The emulsion should remain stable for at least 30 minutes. The antigen-adjuvant emulsion is best injected subcutaneously as a depot.

Example 4

Toxicity studies were performed in mice and rats on the peptide composition of the vaccine in Example 2. The mouse was selected for the study to provide comparative data from a second commonly used rodent species. The test substance was a mixture of four peptides supplied as one vial containing lyophilised material for reconstitution with physiological saline, and dose levels were expressed in terms of total peptide load. The individual peptides was present in ratio 1:1:1:1 w/w giving dose levels of each peptide of 0.0075 mg/kg body weight, 0.075 mg/kg body weight and 0.75 mg/kg body weight, which are up to 500 fold the intended human dose. The test animals were divided into four groups of ten animals each (five males and five females); a saline control group and groups for low, intermediate and high doses. The test composition was administered once, by intravenous infusion into a tail vein at a dose rate of 3 ml/minute. The animals were killed at day 15 and 16 by intraperitoneal injection of sodium pentobarbitone.

The results of these studies indicated that the dose levels administered to the mice and rats elicited no adverse reactions and that the no effect level was in excess of 3 mg/kg.

Example 5

Immunoassay for Detection of Antibodies Induced by HIV-1

The magnetic particle reagents are to be prepared according to the manufacturers recommended protocol. Dynal AS, is the manufacturer of the Dynabeads, which are employed. The magnetic particles coated with ligand are called Reagent 1. A peptide according to the invention is covalently coupled to the pre-activated surface of the magnetic particles. It is also possible to physically absorb the peptide to the surface of the magnetic particles. The concentration of particles in Reagent 1 is within the range from 1 mg/ml to 15 mg/ml. The particle size varies between 0.2 μm to 15 μm. The concentration of peptides is within the range from 0.01 mg/mg particle to 1 mg/mg particle.

The anti-human Ig Alkaline Phosphatase (AP) conjugated antibody reagent is prepared according to the recommended protocol of Dako AS. This protocol is a standard procedure in this field. This reagent is called Reagent 2.

The substrate solution phenolphtalein-monophosphate is to be prepared according to the recommended protocol of Fluka AG. This protocol is a standard procedure in this field. The substrate solution is called Reagent 3.

The washing and incubation buffer which is used is standard 0.05M tris-base buffer with the following additional compounds; Tween 20 (0.01% to 0.1%), glycerol (0.1% to 10%) and sodium chloride (0.2% to 0.1%).

The assay procedure comprises an incubation step wherein 1 drop of Reagent 1 is mixed with 2 drops of washing buffer in each well. After mixing, 30 μl of sample is added and the solution is incubated for 5 minutes. The magnetic particles can be trapped by a magnet and the liquid removed, before the magnet is separated. Then the wells are washed twice in 4 drops of washing solution, before incubation with Reagent 2. 1 drop of Reagent 2 is added with 2 drops of washing buffer and the solution is incubated for 5 minutes. The magnetic particles can be trapped by a magnet and the liquid removed, before the magnet is separated. Then the washing step is repeated before incubation with Reagent 3. 2 drops of Reagent 3 is added to each well and the solution is incubated for 3 minutes. The results can be read against a white background. Positive results are red (3+=strong red) whereas negative results are clearly light yellow/brown solutions as obtained in the negative control.

The immunoassay kit could be used in detection of antibodies, induced either by HIV virus or HIV-specific peptides or proteins, for instance the peptides of the present invention.

The above Examples are only meant as illustrating the invention. It must be understood that a person skilled in the art can modify the peptides, antigens and vaccines herein described without deviating from the concept and scope of this invention as set forth in the claims.

The polypeptides of the invention can be used in a combination of at least one peptide selected from each group of sequences, SEQ ID NOs: 1, 4, 9 and 15 to form antigens and the the active principle of a prophylactic or therapeutic vaccine intended to provide protection against the human immunodeficiency virus type 1 (HIV-1). The vaccine may include compounds having beneficial effects in protecting or stimulating the host's immune system (human being or vertebrate animal) for instance interleukins, interferons, granulocyte macrophage growth factors, haematopoietic growth factors or similar. Preferably the vaccine composition further contain an adjuvant or vehicle, more preferably the adjuvant or vehicle is Monophosphoryl Lipid A (MPL®) possibly with alum, Freund's adjuvant (complete or incomplete) or aluminum hydroxide. The optimal amount of adjuvant/vehicle will depend on the type(s) which is chosen.

The peptide or vaccine formulation can be freeze-dried prior to storage. The vaccine may be stored preferably at low temperature, in ampoules containing one or more dosage units, ready for use. Persons skilled in the art will appreciate that a suitable dose may depend on the body weight of the patient, the type of disease, severity of condition, administration route and several other factors. The vaccine might be administered up to twelve times and through injection, typically it will be administered about six times. In preparation of an injection solution the peptides are dissolved in sterile water or sodium chloride solution at a final concentration of 1-3 mg/ml per peptide and 0-0.9% sodium chloride. Typically an injection volume is 100 μl to 200 μl (2×100 μl). The peptide is preferably co-administered with a suitable adjuvant and/or a granulocyte-macrophage growth factor for instance Leucomax@ Shering Plough. Suitable administration may be intracutane, subcutane, intravenous, peroral, intramuscular, intranasal, mucosal or any other suitable route. Booster administrations may be required in order to maintain protection.

Example 6

The anti-HIV p24 immune response resulting from Vacc-4x immunization could in combination with ART potentially improve immune reconstitution in patients who have not fully regained a healthy CD4 level (>600×10$^6$/L). Potential benefits of Vacc-4x in subjects with incomplete immune reconstitution include a possible sustained improvement in the immune response to p24 and HIV.

Potential risks include the discomfort and inconvenience associated with the immunizations and the risk of known or unknown side effects of exposure to Vacc-4x and Leukine (rhu-GM-CSF) including, most commonly, local reactions at the site of injections and fatigue (likelihood not yet determined).

The results of non-clinical single-dose studies in mice and rats indicate that the dose levels of intravenous Vacc-4x elicited no adverse reactions and that the no effect level was in excess of 3 mg/kg, which constitutes a 500 fold safety margin over the planned human dose level.

In a rabbit study the effect of Vacc-4x was evaluated in the presence of concomitant GM-CSF, the adjuvant used in the clinical program. Local intradermal reactions such as erythema and edema were noted, however, similar effects were noted in control animals both macroscopically and histological. These local reactions were slightly more pronounced in the Vacc-4x treated animals. There were no systemic reactions in this study. These data indicate that Vacc-4x has no limiting toxicology in a model that is relevant to the proposed clinical study.

The therapeutic vaccine candidate Vacc-4x, has been studies in a Phase I and three Phase II clinical studies. The Phase I study enrolled 11 HIV-positive subjects, including nine subjects on ART. Subjects were maintained on ART (if entered on ART); all subjects were treated with 12 immunizations of Vacc-4x at a dose of 0.4 mg/injection over a period of 26 weeks. Immunizations were performed following injection of rhu-GM-CSF (Leucomax®) [molgramostim]) as adjuvant. All subjects experienced one or more adverse events (AEs); nine subjects experienced events judged related to treatment. The adverse reactions reported were mild or moderate in severity except for severe local reactions in one subject. No subjects were withdrawn due to treatment-related AEs or toxicological reactions; no serious adverse events (SAEs) occurred. Treatment related events observed in more than one subject included painful injection (seven subjects), fatigue-vertigo (four subjects), influenza-like symptoms (two subjects), and irritated skin at injection site (two subjects).

All subjects experienced a cell-mediated immune response, measured by delayed-type hypersensitivity (DTH) skin reaction. Some cell-mediated immune response, measured by $\gamma$ IFN release using enzyme-linked immunosorbent spot assay (ELISPOT), was reported for 45% of the subjects; no antibody response to Vacc-4x peptides was observed.

The Phase II dose-finding study (CTN B-HIV 2/2001) enrolled 40 HIV positive subjects, of which 38 completed the trial. Subjects were maintained on ART and treated with 10 immunizations at a dose of 0.4 mg (20 subjects) or 1.2 mg (20 subjects) per Vacc 4x injection, over a period of 26 weeks. Immunizations with Vacc 4x were performed following injection of rhu-GM-CSF (Leucomax [molgramostim]) as a local adjuvant. ART was interrupted from Week 26 to Week 30 to allow exposure to the subject's own virus (autologous immunization). ART was resumed from Week 30 to Week 38 to allow maturation of immune responses to the Vacc 4x peptides and to the subject's own virus. ART was discontinued from Week 38 to Week 52 when the study was formally concluded. Treatment-related AEs were observed in 20 subjects (8 subjects in the 0.4 mg group and 12 subjects in the 1.2 mg group). No SAEs were reported during the period of immunization. One subject experienced a transient vasovagal reaction in conjunction with immunization and the DTH test at Week 26 and Week 38. A second subject experienced a vasovagal reaction in conjunction with the DTH test at Week 52. For the laboratory parameters, vital signs, and performance status, no changes attributable to immunization were observed. Changes in HIV RNA, CD4 cell counts, and CD8 cell counts showed no safety concerns related to immunization.

Immunological responses reported as DTH positive reactions were observed for all subjects. Overall, positive responses both for induration and erythema were statistically significantly higher in the high dose (HD, 1.2 mg Vacc-4x) group compared to the low dose (LD, 0.4 mg Vacc 4x) group. The dose-dependent differences in DTH reactions were maintained throughout the study. T-cell proliferation appeared stable after Week 12 and demonstrated an HD advantage, consistent with the DTH results. ART was interrupted at Week 38 with planned restart when CD4 counts fell to less than 200/µL or when AIDS- or HIV related events were observed (i.e. clinical practice). DTH responses to Vacc-4x (high versus low response determined at Week 38) were associated with reduced viral loads and correspondingly improved CD4 counts at the end of the study (Week 52).

During the immunization period, CD4 counts were stable or increased. Interruption of ART resulted in reduction of CD4 counts. However, 14 weeks after the last interruption of ART (Week 52), the mean CD4 counts were still above 200×106 cells/L. No difference between the LD and the HD groups was observed. The majority of subjects remained off ART following completion of the study (Week 52); permission was given to follow the subjects until they resumed ART. The duration of treatment interruption was linked to immune responsiveness to the peptides. When subjects were compared to similar subjects in the Netherlands that had stopped treatment without Vacc-4x administration, a significantly slower decline in CD4 cells was noted for the Vacc-4x subjects. The median treatment interruption achieved for all the subjects that participated in the Vacc-4x Phase II clinical study was 31 months.

CTN BI Vacc-4x/2009/1 was an open-label follow-up of study CTN B-HIV-2/2001 to determine whether a re-boost with Vacc-4x could reactivate or increase the immune response obtained during the immunization performed in the CTN B-HIV-2/2001 study. The secondary objectives were to evaluate: the in vivo immunogenicity of Vacc-4x by evaluation of DTH and to compare the DTH response to DTH in the initial study; the effect of Vacc-4x on CD4 counts, CD8 counts and HIV viral RNA; and the safety and tolerability of Vacc-4x. All 26 subjects included in the study received two booster administrations of Vacc-4x.

A total of 74 AEs were reported by 23 subjects. Most adverse events (n=60) were scored as possibly/probably related to the study treatment. The majority (98%) of the related adverse events were mild. Two adverse events related to study treatment, one headache and one injection site indurations, were scored as moderate intensity. Itching (injection site pruritus) was the most frequent reported adverse event related to the study treatment. Nineteen patients (73%) reported this adverse event at least once. Ten of these patients reported itching related to both immunizations, while for the other nine patients it was only reported once. Five patients reported swelling related to the immunization. For three of these patients swelling was reported after both immunizations. No patient died during the study. No patient reported serious adverse events and no clinically relevant changes were recorded.

The study demonstrated that Vacc-4x peptides induced T cell responses lasting up to seven years. By re-boosting it was possible to increase killing markers, this again indicates that T cells had increased their potential to kill HIV-infected cells. Before re-boosting, all the patients had returned to CD4, CD8 and viral load levels that were similar to those before ART was stopped in the main study. Re-boosting had no negative effect on the CD4, CD8 and viral load of the patients. No safety concern was reported as a result of the re-boost of these patients.

The Phase II Study CT-BI Vacc-4x 2007/1 (EudraCT Number 2007-006302-13) was performed in US and Europe (UK, Germany, Spain and Italy). The study was a randomized, double-blind, multicenter, immunogenicity study of Vacc-4x versus placebo in patients infected with HIV-1 who have maintained an adequate response to ART. The primary objective was to evaluate the effect of Vacc-4x immunizations versus placebo on CD4 counts, T-cell function (ELISPOT, T-cell proliferative responses and intracellular cytokine staining) and the response to interruption of ART. The necessity to resume ART between the interruption of ART at Week 28 and the end of the study at Week 52, due to decreased CD4 count or increased viral loads, was monitored as one of the primary efficacy endpoints.

In the ITT analysis population, it was concluded that Vacc-4x did not reduce the proportion of subjects requiring resumption of ART after ART cessation at Week 28 in comparison with placebo. There was also no effect compared with placebo on the percentage change in CD4 count between Week 28 and the last CD4 assessment before resumption of ART. The time to restarting ART was similar in Vacc-4x and placebo-treated subjects.

The viral load results after ART cessation varied between subjects with evidence of favourable effects of Vacc-4x immunization over placebo. There were no significant differences in the repeated measures ANOVA for viral load over Weeks 4 to 52 when data included all evaluable subjects, irrespective of whether they were or were not taking ART. In the subgroup of subjects who remained off ART until Week 52, the average viral load was lower in the Vacc-4x-treated subjects than the placebo group. A post-hoc analysis showed the Week 52 (Last Observation Carried Forward [LOCF]) viral load to be statistically significantly lower in the Vacc-4x group than the placebo group.

The analysis of change in HIV-1 RNA from Week 28 through to Week 52 revealed a statistically significant difference between groups in favour of Vacc-4x. The AUC in those who remained off ART at Week 52 was lower in the Vacc-4x group than in the placebo group. A post-hoc analysis showed this difference in AUC to be statistically significant.

No safety concern was raised during this study. The study was supervised by a Data Safety Monitoring Board (DSMB).

Example 7

Test of Peptides Together with IMiDs for Increased Proliferation, Polyfunctionality, IL-2 Secretion and IFN-γ Production Expansion of polyfunctional HIV-specific T-cells upon stimulation with Dendritic Cells, pre-incubated with peptides to be used according to the invention, may be studied by methods described by Keersmaecker et al. (3. Virol., 2012 86:9351-9360) and referenced therein, HIV proteins Gag or Nef, they are incubated with peptides to be used according to the invention, before they are used to stimulate T-cells in a co-culture.

Keersmaecker et al. found that the presence of IMiDs (Lenalidomide (IMiD3; CC-5013) and pomalidomide (IMiD1; CC-4047) during in vitro T-cell stimulation with dendritic cells presenting Gag- or Nef-specific peptides, resulted in a number of improvements in the function of the T-cells. Among these were; polyfunctional HIV specific CD8+ T cells with enhanced lytic capacity, more Gag antigen epitopes recognized and at lower antigen peptide concentrations, reduced proliferation of CD4+ T cells with increased number of polyfunctional CD4+ T-cells, increased IL-2 production by CD8 T-cells, detectable IFN-γ production by CD8+ T-cells and CD4 T-cells after antigen stimulation.

"*Expansion of Polyfunctional HIV-Specific T Cells upon Stimulation with mRNA Electroporated Dendritic Cells in the Presence of Immunomodulatory Drugs*" Brenda De Keersmaecker, Sabine D. Allard, Patrick Lacor, Rik Schots, Kris Thielemans, and Joeri L. Aerts J. Virol. September 2012 86:9351-9360; published ahead of print 20 Jun. 2012, doi:10.1128/JVI.00472-12

Example 8

Suggested Clinical Study Protocol for the Test of Peptide Composition Comprising 4 Peptides in Combination with Lenalidomide and HDAC Inhibitor Immunizations (four primary immunizations and two booster immunizations) at Weeks 1, 2, 3 and 4, and booster immunizations at Weeks 12 and 13 with either:

1) Peptide composition with GM-CSF as adjuvant and Lenalidomide (CC-5013), or
2) Peptide composition with GM-CSF as adjuvant and Placebo for Lenalidomide (CC-5013).
3) Placebo Suggested Doses:
Peptide composition: 0.6, 0.9, 1.2 and 1.5 mg (Equimolar amount of each peptide)
Lenalidomide: 5.10, and 25 mg.
Subjects randomized to the Lenalidomide (CC-5013) arm will take a single oral dose of Lenalidomide (CC-5013) daily the two preceding days before immunization with the Peptide composition and on the day of each immunization.

The Peptide composition used according to this clinical trial setup consists of SEQ ID NO:3, SEQ ID NO:6, SEQ ID NO:11, and SEQ ID NO:18.

At week 20 subjects in all study arms will receive 20 mg panobinostat (LBH589) orally on days 1, 3, and 5 (i.e. 3 times a week) every other week for a period of 8 weeks (up to week 28) while maintaining background ART. This will be followed by a 24 week follow up period (up to week 52). Upon completion of the study, subjects may be invited to participate in an additional observational study in which ART will be interrupted to evaluate the effect of study treatment on virological control. Enrolment into this part of the study will be optional and determined by the effect of study treatments on the latent HIV-1 reservoir. (Maximum duration of treatment interruption: 16 weeks).

In Summary:
Study arm 1: Peptide composition+IMiD+HDAC (panobinostat)
Study arm 2: Peptide composition+HDAC (panobinostat)
Study arm 3: HDAC (panobinostat)

Depletion of the viral reservoir as a result of the combination treatments according to the present invention may be quantified by for instance following the procedures set forth in Lehrman et al. (The Lancet (366), 2005, pp. 549-555) and references there in. In brief, this includes measuring in samples of patient blood obtained before, during and after treatment; p24 expression from stimulated latently infected cells, plasma HIV RNA concentration (viral load), and integrated HIV DNA by realtime PCR analysis.

Example 9

DC/T-Cell Proliferation Assay

Dendritic cells (DC) were generated from monocytes isolated from buffy coat preparations from healthy blood donors. Briefly, peripheral blood mononuclear cells were separated by a density gradient centrifugation and the monocytes were then negatively isolated using the Dynabeads Untouched Human Monocytes (Invitrogen, Carlsbad, Calif.) following the manufacturer's instructions. The monocytes were cultured with IL-4 (20 ng/ml; Immunotools, Friesoythe; Germany) and GM-CSF (100 ng/ml; Immunotools) in X-VIVO15 medium (Lonza, Basel, Switerland) for 5-6 days to generate immature DC. Cytokines were replenished every 2-3 days. The maturation of the cells was performed for 24 hours with IFN-γ (1000 IU/ml), TNF-α (50 ng/ml), IL-1β (25 ng/ml) IFN-α (3000 IU/ml). After maturation, the DC were pulsed for 2 hours at 37° C. with peptides at 10 µg/ml, before extensive washing and co-culture with Peripheral blood mononuclear cells (PBMC) labelled with a fluorescent dye (VPD450, BD biosciences, Sam Jose, Calif.). Various ratios with DC:T cell were tested alongside with appropriate controls. IL-2 (50 U/ml) and IL-7

(50 ng/mL) (Both, Immunotools) and wells with or without IMiDs were added at the start of co-culture. At day 6-10, the level of T cell proliferation was analysed by flow cytometry. The supernatants from the co-culture wells were investigated with Luminex technology to establish any suppressor activity.

Example 10

The peptides according to the invention used in the following examples were synthesized by Schafer-N as c-terminal amides using the Fmoc-strategy of Sheppard, (1978) J. Chem. Soc., Chem. Commun., 539.

Cell Penetration Assay

Intracellular Staining for Biotinylated Peptides 96-well U-bottom polystyrene plates (NUNC, cat no: 163320) were used for staining of human PBMCs. Briefly, 8 ul of N- or C-terminally biotinylated peptides according to the invention (i.e. 5 mM, 2.5 mM & 1.25 mM tested for each peptide) were incubated at 37° C. for 2 h with 40 ul of PBMC (12.5×106 cells/ml) from blood donors. Cells were then washed 3× with 150 ul of Cellwash (BD, cat no: 349524), followed by resuspension of each cell pellet with 100 ul of Trypsin-EDTA (Sigma, cat no: T4424), then incubated at 37° C. for 5 min. Trypsinated cells were then washed 3× with 150 ul of Cellwash (BD, cat no: 349524), followed by resuspension with BD Cytofix/Cytoperm™ plus (BD, cat no: 554715), then incubated at 4° C. for 20 min according to manufacturer. Cells were then washed 2× with 150 ul PermWash (BD, cat no: 554715). Cells were then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3× with 150 ul PermWash, followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

Extracellular Staining for Biotinylated Peptides 96-well U-bottom polystyrene plates (NUNC, cat no: 163320) were used for staining of human PBMCs. Briefly, 8 ul of N- or C-terminally biotinylated peptides according to table 1 or table 2 (i.e. 5 mM, 2.5 mM & 1.25 mM tested for each peptide; all peptides manufactured by solid phase synthesis by commercial suppliers) were incubated at 37° C. for 2 h with 40 ul of PBMC (12.5×106 cells/ml) from blood donors. Cells were then washed 3× with 150 ul of Cellwash (BD, cat no: 349524), then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3× with 150 ul of Cellwash (BD, cat no: 349524), followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

It was clearly seen that the CMI peptides according to the invention had improved ability to enter the cell compared to its native counterparts The data are geomean-value of each testet peptide, as calculated by the FACS Duva software. The Geomean values by trypsinating/Cytofix/Cytoperm:

Example 11

Positive CTL response may alternatively be assayed by ELISPOT assay.

Human IFN-Gamma Cytotoxic T-Cell (CTL) Response by ELISPOT Assay

Briefly, at day 1, PBMC samples from HCV patients were incubated in flasks (430 000 PBMCs/cm2) for 2 h at 37° C., 5% CO2 in covering amount of culture media (RPMI 1640 Fisher Scientific; Cat No. PAAE15-039 supplemented with L-Glutamine, (MedProbe Cat. No. 13E17-605E, 10% Foetal Bovine serum (FBS), Fisher Scientific Cat. No. A15-101) and Penicillin/Streptomycin, (Fisher Acientific Cat. No. P11-010) in order to allow adherence of monocytes. Non-adherent cells were isolated, washed, and frozen in 10% V/V DMSO in FBS until further usage. Adherent cells were carefully washed with culture media, followed by incubation at 37° C. until day 3 in culture media containing 2 µg/ml final concentration of hrGM-CSF (Xiamen amoytop biotech co, cat no: 3004.9090.90) & 1 µg/ml hrIL-4 (Invitrogen, Cat no: PHC0043) and optionally an immunomodulationg agent (IMiD), and this procedure was then repeated at day 6. At day 7, cultured dendritic cells (5 000-10 000 per well) were added to ELISPOT (Millipore multiscreen HTS) plates coated with 0.5 µg/well anti-human γ Interferon together with thawed autologous non-adherent cells (200 000 per well), antigen samples (1-8 ug/ml final concentration for peptide antigens; 5 ug/ml final concentration for Concanavalin A (Sigma, Cat no: C7275) or PHA (Sigma, Cat no: L2769)) & anti-Anergy antibodies (0.03-0.05 ug/ml final concentration for both anti-PD-1 (eBioscience, cat no: 16-9989-82) & anti-PD-L1 (eBioscience, cat no: 16-5983-82)). Plates were incubated overnight and spots were developed according to manufacturer. Spots were read on ELISPOT reader (CTL-ImmunoSpot® S5 UV Analyzer).

Example 12

ELISPOT Assay

At day one, PBMC samples from blood donors were thawed, washed with warm medium and incubated in flasks (250000 PBMCs/cm2) for 24 hours at 37° C., 5% CO2 in covering amount of culture media (RPMI 1640 with ultraglutamine, Lonza, BE12-702F701; 10% Foetal Bovine serum (FBS), Fisher Scientific Cat. No. A15-101; Penicillin/Streptomycin, Fisher Scientific Cat. No. P11-010) to allow the cells to recover after thawing. At day two, the cells were added to a Falcon Microtest Tissue Culture plate, 96 well flat bottom, at 500 000 cells per well in a volume of 200 µl total medium. Parallel wells were added the indicated stimuli in duplicate and optionally an immunomodulationg agent (IMiD), or left with medium as a control for 6 days at 37° C., 5% $CO_2$. After the six days of incubation, 100 µl of the cell suspension were transferred to an ELISPOT (Millipore multiscreen HTS) plate coated with 1 µg/ml native influenza M2e protein. After a 24 hour incubation, the plate was washed four times with PBS+0.05% Tween20, and a fifth time with PBS, 200 µl/well. A mouse Anti-human IgG or IgM biotin (Southern Biotech 9040-08 and 9020-08) was diluted in PBS with 0.5% FBS and incubated for 90 minutes at 37° C. The washing was repeated as described, before 80 µl Streptavidin-Alkaline-Phosphatase (Sigma Aldrich, S289) was added each well and incubated at 60 minutes in the dark, at room temperature. The wells were then washed 2 times with PBS+0.05% Tween20 and 4 times with PBS, 200 µl/well, before the substrate, Vector Blue Alkaline Phosphatase Substrate kit III (Vector Blue, SK-5300) was added and let to develop for 7 minutes at room temperature. The reaction was stopped with running water, the plates let dry and the sport enumerated by an ELISPOT reader (CTL-ImmunoSpot®) S5 UV Analyzer).

ELISA

100 µl of antigen as indicated (pre-incubated in Coating buffer—0.05M $Na_2CO_3$ pH9.6; denoted CB—in cold at 8 µg/ml 1-3 days) or just CB (background control) was used for coating wells in microtiter plates at 4° C. The microtiter plates are then washed 3× with washing buffer (PBS+1% v/v Triton-X100; denoted WB), followed by 2 h blocking at room temperature (RT) with 200 µl/well of blocking buffer (PBS+1% w/v BSA). Plates are then washed 3× with WB, followed by 1 h incubation at 37° C. with 50-70 µl/well of added human (or rabbit or sheep) sera (serial dilutions ranging from 1:5-1:250 in dilution buffer (PBS+1% v/v Triton-X100+1% w/v BSA; denoted DB)). Plates are then washed 6× with WB, followed by 1 h incubation at RT with 70 µl/well of Alkaline Phosphatase-conjugated Protein G (3 µg/ml in DB; Calbiochem 539305) or goat anti-mouse IgG biotin (1 µg/ml, Southern Biotech, 1030-08. In case of the goat anti-mouse IgG biotin, the plates were washed one extra step as described, before addition of 100 µl Strepta-vidin-Alkaline-Phosphatase (1 µg/ml, Sigma Aldrich, S289) and incubated 1 hour at RT. Plates are then washed 6× with WB, followed by 10-60 min incubation at room temperature with 100 µl/well of 0.3% w/v of Phenophtalein monophosphate (Sigma P-5758). Plates are finally quenched by adding 100 µl/well of Quench solution (0.1M TRIS+0.1M EDTA+0.5M NaOH+0.01% w/v $NaN_3$; pH14), followed by a measurement with a ELISA reader (ASYS UVM 340) at 550 nm. The strength of the sera, i.e. the magnitude of the humoral immune response, is then reported as the dilution of sera that result in the described Optical Density (OD) value, or the OD value at the indicated dilution of sera.

Example 12

Clinical Trial Protocol

Phase I/IIa Study to Evaluate the Effect of Therapeutic HIV-1 Immunization Using Vacc-4x+rhuGM-CSF, and HIV-1 Reactivation Using Romidepsin, on the Viral Reservoir in Virologically Suppressed HIV-1 Infected Adults on cART.

The primary objective is to measure the effect of treatment with Vacc-4x+rhuGM-CSF and cyclic romidepsin treatment on the HIV-1 latent reservoir in HIV-infected patients virologically suppressed on cART.

Endpoints:
Primary Endpoints:
1) Safety and tolerability evaluation as measured by adverse events (AE), adverse reactions (AR), serious adverse events (SAE), serious adverse reactions (SAR), serious unexpected adverse reactions (SUSAR)
2) Latent reservoir size measured in CD4+ T cells by:
a) HIV-1 viral outgrowth assay (HIV-1 RNA per 106 in resting memory CD4+ T cells (RUPM))
b) Integrated HIV-1 DNA (copies per 106 CD4+ T cells)
c) Total HIV-1 DNA (copies per 106 CD4+ T cells)

Secondary Endpoints PART B
1) Time to re-initiation of cART
2) Time to detectable viremia during cessation of cART
3) HIV transcription measured as cell associated unspliced HIV-1 RNA (copies per $10^6$ CD4+ T cells)
4) HIV-specific T-cell responses as measured by ELISpot, proliferation and/or intracellular cytokine staining
5) Plasma HIV-1 viral load
6) Histone H3 acetylation as measured in lymphocytes
7) T cell count and phenotype
8) Antibody titer to Vacc-4x peptides and to p24 as measured by ELISA.

An Open Phase I/IIa Study to Evaluate the Effect of Therapeutic HIV-1 Immunization using Vacc-4x+rhuGM-CSF, and HIV-1 Reactivation using Romidepsin, on the Viral Reservoir in Virologically Suppressed HIV-1 Infected Adults on cART. The study is conducted to evaluate the safety/tolerability of Vacc-4x+rhuGM-CSF as adjunctive therapy to romidepsin and to assess the impact on the latent HIV reservoir and the ability to control viral load during an Analytical Treatment Interruption (n=20, ie. 20 patients).

Target Population: Virologically suppressed (pVL<50 copies/mL) HIV-1 infected adults currently on cART.

Study Procedures/Frequency:
1. A pre-treatment phase of 4 weeks (visit 1 to visit 2) to confirm the stability of the latent HIV-1 reservoir and determine baseline HIV-1 T lymphocyte specific immunity.
2. A therapeutic HIV-1 immunization phase of 12 weeks (from visit 2 to visit 7) in which Vacc-4x will be administered together with rhuGM-CSF at visit 2, 3, 4, 5, 6 and 7 follow by a follow-up period of 2 weeks (visit 8-visit 9).
3. A viral reactivation phase of 3 weeks (visit 10-visit 12) consisting of one cycle of romidepsin infusions at a dosing of 5 mg/m2.
A post-treatment observation phase of ~8 weeks (visit 13-visit 14) to assess the effect of the investigational treatment on the size of the latent HIV-1 reservoir.
5. An Analytical Treatment Interruption phase of 16 weeks (from after visit 15-34).

Investigational Medicinal Products:
Vacc-4x: 1.2 mg administered intradermally at day 0, 7, 14, 21, 77 and 84 (visit 2, 3, 4, 5, 6 and 7)
rhuGM-CSF: Leukine® (Sanofi) 0.06 mg administered intradermally, 10 min prior to Vacc-4x administration, at day 0, 7, 14, 21, 77 and 84 (visit 2, 3, 4, 5, 6 and 7)
Romidepsin: Istodax® (Celgene) 5 mg/m2 administered by 3 intravenous infusion in three consecutive weeks (day 105, 112 and 119) (visit 10, 11b and 12) (corresponding to one 28 day cycle).

Trial Design:
1. A pre-treatment phase of 4 weeks (visit 1 to visit 2) to confirm the stability of the latent HIV-1 reservoir and determine baseline HIV-1 T lymphocyte specific immunity.
2. A therapeutic HIV-1 immunization phase of 12 weeks (2 to visit 7) in which Vacc-4x will be administered together with rhuGM-CSF at visit 2, 3, 4, 5, 6 and 7 followed by a follow-up period of 2 weeks (visit 8 to visit 9).
3. A viral reactivation phase of 3 weeks (visit 10 to visit 12) consisting of one cycle of romidepsin infusions at a dosing of 5 mg/m2.
4. A post-treatment observation phase of 8 weeks (visit 13 to visit 14) to assess the effect of the romidepsin on the size of the latent HIV-1 reservoir.
5. An Analytical Treatment Interruption phase of 16 weeks (visit 15-34).

Treatment
Vacc-4x
Vacc-4x, consists of four synthetic peptides (Vacc-10 acetate, Vacc-11 acetate, Vacc-12 acetate, and Vacc-13 acetate), each corresponding to conserved domains on the HIV-1 p24 capsid protein representing the native Gag regions with residues 166-185, 252-269, 264-284, and 335-354, respectively.

Vacc-4x is manufactured in accordance with Good Manufacturing Practice (GMP) and is supplied as sterile vials of freeze-dried white powder. There is no additional ingredient in the product.

RhuGM-CSF (sargramostim, Leukine®, Sanofi)

Leukine® is manufactured by Sanofi and supplied by Genzyme. It is a glycoprotein of 127 amino acids characterized by three primary molecular species having molecular masses of 19,500, 16,800 and 15,500 daltons. The liquid Leukine® presentation is formulated as a sterile, preserved (1.1% benzyl alcohol), injectable solution (500 mcg/mL) in a vial. Lyophilized Leukine® is a sterile, white, preservative-free powder (250 mcg) that requires reconstitution with 1 mL Sterile Water for Injection, USP or 1 mL Bacteriostatic Water for Injection, USP. Liquid Leukine® has a pH range of 6.7-7.7 and lyophilized Leukine® has a pH range of 7.1-7.7.

For further information refer to IB (Leukine® prescribing information).

Romidepsin (Istodax®, Celgene)

Istodax® is manufactured by Celgene Corporation. This histone deacetylase (HDAC) inhibitor is a bicyclic depsipeptide. At room temperature, romidepsin is a white powder and is described chemically as (1S,4S,7Z,10S,16E,21R)-7-ethylidene-4,21-bis(1-methylethyl)-2-oxa-12,13-dithia-5,8,20,23-tetraazabicyclo[8.7.6]tricos-16-ene-3,6,9,19,22-pentone. The empirical formula is $C_{24}H_{36}N_4O_6S_2$. Istodax® is supplied as a kit containing two vials. Istodax® (romidepsin) for injection is a sterile lyophilized white powder and is supplied in a single-use vial containing 10 mg romidepsin and 20 mg povidone, USP. Diluent for Istodax® is a sterile clear solution and is supplied in a single-use vial containing a 2-mL deliverable volume. Diluent for Istodax® contains 80% (v/v) propylene glycol, USP and 20% (v/v) dehydrated alcohol, USP.

For further information refer to IB for romidepsin.

Vacc-4x

Each dose of Vacc-4x (0.1 mL of a 12 mg/mL solution), will be administered by intradermal injections following the intradermal administration of rhuGM-CSF (Leukine®) as adjuvant. A total of 6 Vacc-4x/rhuGM-CSF immunizations (visit 3, 4, 5, 6, 7 and 8) are planned in the HIV-1 therapeutic vaccination phase.

Approximately 10 minutes before each administration of Vacc-4x, rhuGM-CSF will be administered intradermally as an adjuvant. Vacc-4x must be administered intradermally at the same site as rhuGM-CSF, superficial to the deltoid muscle and in the same arm during the course of the study. When administering the intradermal injection, utmost care must be taken so that no material is injected subcutaneously. If administered correctly, after puncture of the skin a small bleb should appear following the injection of only a small amount of product. An injection that is too superficial should be avoided as this will result in loss of the sample volume from the injection site during injection or after withdrawal of the needle.

RhuGM-CSF

Each dose of rhuGM-CSF (0.1 mL of 0.60 mg/mL solution) will be administered as an adjuvant by intradermal injection 10 minutes prior to the intradermal administration of Vacc-4x immunizations (visit 3, 4, 5, 6, 7 and 8) during the HIV-1 therapeutic vaccination phase. rhuGM-CSF must be administered intradermally at the same site as Vacc-4x, superficial to the deltoid muscle and in the same arm during the entire course of the study.

When administering the intradermal injection, utmost care must be taken so that no material is injected subcutaneously. If administered correctly, after puncture of the skin a small bleb should appear following the injection of only a small amount of product. An injection that is too superficial should be avoided as this will result in loss of the sample volume from the injection site during injection or after withdrawal of the needle.

Romidepsin

The dose is 5 mg/m2 administered intravenously over a 4 hour period on Days 1, 8, and 15 of a 28-day cycle (visit 10, 11 and 12).

Trial Assessment:

Laboratory Assessment

Biochemistry:

Routine biochemistry includes haematology parameters (haemoglobin, total and differential leukocyte count, platelet count), ALAT, bilirubin, alkaline phosphatase, creatinine, sodium, potassium, phosphorus, magnesium, calcium, urea, albumin and CRP.

HIV Virology:

HIV-1 viral outgrowth (HIV-1 RNA per $10^6$ resting memory CD4+ T cells (RUPM)): The gold standard assay used to measure the frequency of resting CD4+ T cells carrying latent but replication competent virus is based on co-culture of highly purified resting CD4+ T cells from the patient together with PBMCs from an HIV-negative donor and is measured as infectious units per million cells (IUPM) [Finzi 1999, Chun 2007].

Integrated HIV-1 DNA (copies per $10^6$ CD4+ T cells): Within infected cells, HIV DNA can exist as linear non-integrated forms, circular forms and as an integrated provirus. In patients receiving effective cART, the majority of HIV DNA is integrated in resting latently infected CD4+ T cells. The most widely used technique to quantify the number of cells that contain integrated virus is the Alu-LTR PCR assay [Sonza 1996].

Total HIV-1 DNA (copies per $10^6$ CD4+ T cells): Total HIV DNA quantifies integrated and non-integrated DNA as well as latent and defective virus. There is a strong correlation between total HIV DNA and integrated HIV DNA in patients on cART and therefore cell-associated HIV DNA is likely to be a good surrogate marker of the total number of latently infected cells [Koelsch 2008].

Unspliced HIV-1 RNA (copies per $10^6$ CD4+ T cells): HIV transcription is measured as copies of cell-associated unspliced HIV-1 RNA/106 CD4+ T cells using digital droplet PCR Plasma HIV-1 RNA detection by NAT screen: Measured by a transcription mediated amplification (TMA)-based methodology, usually referred to as a nucleic acid test (NAT)-screen (PROCLEIX ULTRIO Plus, Genprobe).

Plasma HIV RNA, quantitative viral load: Measured by Roche VL (routine clinical assay) Histone H3 acetylation: Measured in lymphocytes using flow cytometry with intracellular cytokine stain on fresh isolated PBMCs.

T Cell count (CD4 and CD8)

Phylogenetic Analysis

Immunology:

HIV-specific T cell response as measured by ELISpot, proliferation and/or intracellular cytokine staining.

Example 13

Below is presented the viral reactivation data from Part A of the clinical trial "Safety and Efficacy of the Histone Deacetylase Inhibitor Romidepsin and the Therapeutic Vaccine Vacc-4x for Reduction of the Latent HIV-1 Reservoir (REDUC)" (http://clinicaltrials.gov, NTCO2092116).

The inclusion criteria for the study was: Age >18 years, Currently receiving cART and having received cART for a minimum of 1 year, HIV-1 plasma RNA<50 copies/mL for at least 1 year (excluding viral load blips) and CD4 T cell count 500 cells/mm$^3$.

Exclusion Criteria for the study was: CD4 T cell count nadir <200 cells/mm$^3$, Previous treatment with an HDACi (Histone deacetylase inhibitor) within the previous 6 months, Any evidence of an active AIDS-defining opportunistic infection, active HBV or HCV co-infection, significant cardiac disease, malignancy, transplantation, insulin dependent diabetes mellitus or other protocol defined excluded medical condition, Use of any protocol defined contraindicated medication or vaccination, Unacceptable values of the hematologic and clinical chemistry parameters as defined in the protocol. Males or females who are unwilling or unable to use protocol defined methods of contraception.

Part A of the clinical study contained three phases. First, a pre-treatment phase of 2-4 weeks (visit 1-visit 2a) to confirm the stability of the latent HIV-1 reservoir and determine baseline HIV-1 T lymphocyte specific immunity. Second, a viral reactivation phase of 3 weeks (visit 2 to visit 7) consisting of one cycle of romidepsin infusions at a dosing of 5 mg/m$^2$ administered intravenously over a 4 hour period. De-escalation down to 2.5 mg/m$^2$ was planned in case of dose-limiting toxicity was observed. Romidepsin was infused on days 0, 7, and 14. Third, a post-activation phase of ~9 weeks (visit 8 to visit 11) to assess the effect of romidepsin on the size of latent HIV-1I reservoir.

The primary objective of this part of the study was to evaluate the safety and tolerability of romidepsin at a reduced dosing of 5 mg/m$^2$ in HIV-infected patients. The secondary objective was to determine the effect of romidepsin treatment on HIV-1 transcription in HIV-infected patients virologically suppressed on cART.

The primary endpoint of this part was safety and tolerability; evaluation as measured by adverse events (AE), adverse reactions (AR), serious adverse events (SAE), serious adverse reactions (SAR), serious unexpected adverse reactions (SUSAR).

The secondary endpoints in this part of the clinicals study were:
1) HIV transcription measured as cell associated unspliced HIV-1 RNA (copies per 10$^6$ CD4+ T cells)
2) HIV transcription measured as plasma HIV RNA (by NAT screen and standard HIV RNA)
3) Histone H3 acetylation in lymphocytes
4) Size of the latent HIV-1 reservoir in CD4+ T cells as measured by
a) HIV-1 viral outgrowth assay (HIV-1 RNA per 106 in resting memory CD4+ T cells (RUPM))
b) Integrated HIV-1 DNA (copies per 106 CD4+ T cells)
c) Total HIV-1 DNA (copies per 106 CD4+ T cells)

Histone H3 acetylation was measured in lymphocytes using flow cytometry with intracellular cytokine staining on fresh isolated PBMCs. Freshly isolated PBMC's were fixated, permeabilised and stained with acetylation-specific antibodies, providing the possibility to evaluate epigenetic modifications on Histones (Rigby L, Muscat A, Ashley D, Algar E. Epigenetics 2012; 7(8):875-882). Briefly, PBMCs (1×10$^6$) were resuspended in 3 ml ice-cold PBS/1% FBS and centrifuged, then vortexed to dissolve pellet and fixative added, 100 µl 2% PFA (ice-cold), vortexed briefly and incubated on ice for 15 min. Cells were then washed in 4 ml PBS, resuspend in 200 µl PBS and stored at 4° C. until staining. Samples were washed with 3 ml FACS buffer and vortexed to dissolve cell pellet prior to adding 100 µl 0.2% Triton X-100, vortex briefly and incubate for 10 min. at room temperature (RT). Samples were then washed with FACS buffer, 600 µl Block (PBS/10% FBS) was added, sample vortexed to resuspend cell pellet and incubate for 20 min at RT. After washing with 3 ml FACS buffer 5 µl primary antibody Anti-acetyl histone H3 (rabbit) at 200 µg/ml (Merck Millipore) or isotype control at 200 µg/ml (normal rabbit serum, LifeTechnologie) was added, and samples vortexed to resuspend cell pellet, and incubated for 1 hour at RT. Following this samples conjugated donkey anti-rabbit IgG, conc. 120 µg/ml), vortexed to resuspend cell pellet and incubated for 1 hour in the dark (RT). Finall samples were washed with FACS buffer and resuspended in 80 µl PBS and analyzed by FACS (50 000 events, anti-acetyl histone H3 Median Fluorescence Intensity, MFI, calculated by subtracting background MFI from isotype control).

HIV transcription was measured as copies of cell-associated unspliced HIV-1 RNA/106 CD4+ T cells using digital droplet PCR. CD4+ T-cells were isolated from PBMCs using Miltenyi Biotec negative bead separation kit (CD4 T cell isolation, #130-096-533) as described with LD separation columns, lysed (Lysis buffer from Qiagen DNA/RNA extraction kit), and stored ad −80° C. until extraction of RNA and DNA (Allprep isolation kit, Qiagen). Reverse transcription, amplification and quantitation of cell-associated unspliced HIV RNA from HIV patients was performed as follows. In summary, HIV unspliced RNA was detected on the BioRad QX100 droplet digital platform using a defined primer/probe set and related to total cell input by quantitation of the IPO8 (Importin 8) and TBP (Tata Binding Protein) gene transcription. A mixture of 11.5 µl patient extracted mRNA in nuclease-free dH, 1 µl 10 mM dNTP U1240 (Promega), 0.5 µl 3 µg/µl Random hexamers (Applied Biosystems) and 0.5 µl of 0.5 µg/µl Oligo(dT)12-18 Primer (Invitrogen) was prepared, incubated at 65° C. for 5 min, and then immediately on ice for 5 min. First-strand cDNA production was performed by adding a mixture of 4.0 µl 5× First Strand Buffer (Invitrogen), 1.0 µl 0.1M DTT (Invitrogen), 0.5 µl RNAseOUT RNAse inhibitor (40 U/µl, Invitrogen), 1.0 µl Superscript III Reverse Transcriptase (200 U/µl, Invitrogen) for a total reaction volume of 20 µl and incubating at 42° C. for 45 min, then 80° C. for 15 min in a PCR machine. The reaction was held at at 4° C. or on ice until performing the downstream assay. For usRNA a ddPCR mixture was made containing: 3 µl Primer/probe mix SL30M (primers SL19/20 final concentration 1000 nM and MGB probe SL30MIDDLE 5'-TACTCACCAGTCGC-CGC-3 final concentration 250 nM) [Lewin, Journal of Virology 1999; 73(7):6099-6103, Saleh, Retrovirology 2011; 8:80.], 11 µl 2×dPCR Supermix (BioRad), 5 µl Water, and 3 µl cDNA from patient samples (Total vol 22 µl). To adjust for the total cellular input in each sample, relative copy numbers were normalized to two human endogenous control genes TBP PL (VIC) assay ID: Hs00183533_m1 and IPO8 (FAM) assay ID: Hs00427620_m1 (TaqMan gene expression assay, LifeTechnologies, Denmark). All HIV RT samples were run in six replicates while the reference genes were assayed in duplicate. The PCR reaction mixture was loaded into the BioRad QX-100 emulsification device fractionating each sample into 20,000 nanoliter-sized droplets following the manufacturer's instructions. PCR cycling conditions were as follows: 95° C. for 10 min, followed by 40 cycles of a 30 second denaturation at 95° C. followed by a 59° C. extension for 60 seconds and a final 10 minutes at 98° C. After cycling droplets were subsequently read automatically by the QX100 droplet reader (BioRad) and the data was analyzed with the QuantaSoft™ analysis software (BioRad). On average the six HIV replicates generated 80.000-98.000 droplets to be analyzed per time point.

Plasma HIV RNA, quantitative viral load, was measured by Cobas® TaqMan® HIV-1 Test, v2.0 (Roche) according the manufacturer's instruction (routine clinical assay). The lower limit of quantification for this assay is 20 copies HIV-1 RNA/mL, but it provides a qualitative assessment below this. Plasma HIV-1 RNA was also measured by a transcription mediated amplification (TMA)-based methodology, usually referred to as a nucleic acid test (NAT)-screen (PROCLEIX ULTRIO Plus, Genprobe), according to manufacturers instructions.

Results

The objective of part A of the study was to establish the optimal dose of the HDACi Istodax® (romidepsin) based on safety and the effect on HIV reactivation. Treatment with 5 mg/m² of romidepsin was successfully able to reactivate HIV in 6 patients while on conventional HIV medication cART. Both cell-associated un-spliced HIV RNA as well as extracellular HIV RNA were significantly increased as a result of romidepsin infusion. The treatment was safe and most adverse events (AEs) were of grade 1. Two grade II AEs in one individual were observed. No serious adverse events were observed.

Lymphocyte histone H3 acetylation, a cellular measure of the pharmacodynamic response to romidepsin, increased rapidly (maximum fold range: 3.7-7.7 relative to baseline) following each romidepsin administration. Concurrently, HIV-1 transcription (cell-associated un-spliced HIV-1 RNA) increased significantly from baseline (fold range: 2.4-5.0 after third infusion; p=0.03, Wilcoxon). Remarkably, plasma HIV-1 RNA increased from <20 copies/mL at baseline to readily quantifiable levels (using a standard clinical assay) at multiple post-infusion time-points in 5 of 6 patients (range 46-103 copies/mL following the second infusion,). Plasma HIV-1 RNA was also detected more frequently by a transcription-mediated amplification assay at post-infusion time-points compared with baseline.

Visit Schedule:

| Visit | 1 | 2A | 2B | 3 | 4 | 5A | 5B | 6 | 7A | 7B | 8 | 9 | 10 | 11 |
|---|---|---|---|---|---|---|---|---|---|---|---|---|---|---|
| Day | −21 | 0 | 0+4 h | 1 | 3 | 7 | 7+4 h | 10 | 14 | 14+4 h | 17 | 21 | 56 | 84 |

Histone Acetylation:

| | ID | | | | | | | |
|---|---|---|---|---|---|---|---|---|
| Visit | 1101 | 1102 | 1103 | 1105 | 1106 | 1107 | Mean | SEM |
| 2A | 1181 | 1258 | 562 | 1020 | 309 | 372 | 783.6667 | 156.5809 |
| 2B | 3493 | 1534 | 3481 | 2473 | 2360 | 2463 | 2634 | 278.6639 |
| 3 | 3465 | 2197 | 2451 | 2216 | 2475 | 1757 | 2426.833 | 212.5666 |
| 4 | 3102 | 2964 | 3201 | 4130 | 3302 | 2767 | 3244.333 | 176.0919 |
| 5A | 2065 | 2740 | 1284 | 2042 | 2863 | 596 | 1931.667 | 322.9299 |
| 5B | 5363 | 4597 | 4059 | 3198 | 4239 | 2214 | 3945 | 411.2863 |
| 6 | 2788 | 4124 | 3402 | 3859 | 3748 | 3280 | 3533.5 | 177.7932 |
| 7A | 2486 | 3236 | 1789 | 1794 | 1438 | 1211 | 1992.333 | 278.3314 |
| 7B | 7228 | 3580 | 3317 | 4101 | 5467 | 3444 | 4522.833 | 574.7988 |
| 8 | 3875 | 4502 | 3147 | ND | 3675 | 3572 | 3754.2 | 198.1877 |
| 9 | 741 | 2416 | 1607 | 1923 | 1179 | 2467 | 1722.167 | 255.3591 |
| 10 | 1733 | 3579 | 2622 | 3035 | 1592 | 1865 | 2404.333 | 299.3704 |
| 11 | 1243 | 1823 | 1292 | 1287 | 1059 | 970 | 1279 | 110.7231 |

(ND not determined)

CA US HIV RNA HIV RNA copies/10^6 CD4+ T cells:

| | ID | | | | | | | |
|---|---|---|---|---|---|---|---|---|
| Visit | 1101 | 1102 | 1103 | 1105 | 1106 | 1107 | Mean | SEM |
| 1 | 5.4 | 19.7 | 9.7 | 4.8 | 15.9 | 8.7 | 10.7 | 2.2 |
| 2A | 13.3 | 16.8 | 7.4 | ND | 14.5 | 4.5 | 11.3 | 2.1 |
| 2B | 23.0 | 21.7 | 15.7 | 6.2 | 18.7 | 7.6 | 15.5 | 2.7 |
| 3 | 16.7 | 33.8 | 9.5 | 7.3 | 29.4 | 10.3 | 17.8 | 4.2 |
| 4 | 26.4 | 36.2 | 7.5 | 6.8 | 12.1 | 6.6 | 15.9 | 4.6 |
| 5A | 12.5 | 13.7 | 11.3 | 7.6 | 18.9 | 6.6 | 11.8 | 1.7 |
| 5B | 33.7 | 43.3 | 24.8 | 24.0 | 45.2 | ND | 34.2 | 4.0 |
| 6 | 21.3 | 29.0 | 10.4 | 9.1 | 14.4 | 7.9 | 15.3 | 3.1 |
| 7A | 13.3 | 24.2 | 9.9 | 6.0 | 18.1 | ND | 14.3 | 2.8 |
| 7B | 36.5 | 51.9 | 21.0 | ND | 76.0 | 20.5 | 41.2 | 9.3 |
| 8 | 17.4 | 17.8 | 4.2 | ND | 14.9 | 8.9 | 12.7 | 2.4 |
| 9 | 16.4 | 19.0 | 4.6 | 5.2 | ND | 11.1 | 11.3 | 2.6 |
| 10 | 17.9 | 25.0 | 7.6 | 6.2 | 16.8 | 9.3 | 13.8 | 2.7 |
| 11 | 22.0 | 32.7 | 11.2 | 8.0 | 35.1 | 12.2 | 20.2 | 4.3 |

(ND not determined)

HIV VL: HIV RNA copies/mL plasma

| | ID | | | | | |
|---|---|---|---|---|---|---|
| Visit | 1101 | 1102 | 1103 | 1105 | 1106 | 1107 |
| 1 | LOQ | 40 | LOD | LOD | LOQ | LOQ |
| 2A | LOD | LOD | LOD | LOD | LOD | LOD |
| 2B | LOQ | LOD | LOD | LOD | LOD | LOD |
| 3 | 26 | LOD | LOQ | LOD | 27 | LOQ |
| 4 | LOQ | 32 | LOD | LOD | LOD | LOD |
| 5A | LOQ | LOD | LOD | LOD | LOD | LOD |
| 5B | 21 | LOD | 54 | LOQ | LOD | LOD |
| 6 | 59 | 74 | LOQ | LOD | 46 | 103 |
| 7A | LOD | LOD | LOD | LOD | LOD | LOQ |
| 7B | LOQ | LOD | LOD | LOD | LOD | LOD |
| V8 | 22 | LOD | LOD | . | LOQ | 119 |
| 9 | LOQ | LOQ | LOD | LOD | LOD | LOQ |
| 10 | LOD | LOD | 42 | LOD | LOQ | LOQ |
| 11 | LOQ | LOD | 68 | LOD | LOD | LOD |

LOD = "undetectable" HIV RNA,
LOQ = "detectable" not quantifiable HIV RNA<20 c/mL.

TMA assay, presence of HIV RNA:

|  | Subject ID | | | | | | |
| --- | --- | --- | --- | --- | --- | --- | --- |
|  | 1101 | 1102 | 1103 | 1105 | 1106 | 1107 | Percent positive |
| Visit 1 | 1 | 1 | 0 | 1 | 0 | 0 | 50% |
| Visit 2A | 1 | 1 | 1 | 0 | 0 | 0 | 50% |
| Visit 2B | 1 | 0 | 1 | 0 | 1 | 1 | 67% |
| Visit 3 | 1 | 0 | 1 | 1 | 1 | 1 | 83% |
| Visit 4 | 1 | 1 | 1 | 1 | 0 | 1 | 83% |
| Visit 5A | 1 | 1 | 0 | 0 | 0 | 1 | 50% |
| Visit 5B | 1 | 1 | 1 | 1 | 1 | 1 | 100% |
| Visit 6 | 1 | 1 | 1 | 1 | 1 | 1 | 100% |
| Visit 7A | 1 | 1 | 0 | 0 | 0 | 1 | 50% |
| Visit 7B | 1 | 1 | 0 | 1 | 0 | 1 | 67% |
| Visit 8 | 1 | 1 | 1 | . | 1 | 1 | 100% |
| Visit 9 | 0 | 1 | 0 | 1 | 0 | 0 | 33% |

0 = negative (HIV RNA in plasma not detected (by TMA))
1 = positive (HIV RNA in plasma detected (by TMA))

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. A method for reducing latent reservoir size of human immunodeficiency virus type 1 (HIV-1) in a subject infected with HIV-1, the method comprising the steps of:
   a) a therapeutic HIV-1 immunization phase consisting of administering in one or more doses of an effective amount of at least four HIV-specific peptides comprising the amino acid sequences SEQ ID NO: 18 (Vacc-10), SEQ ID NO: 11 (Vacc-11), SEQ ID NO: 6 (Vacc-12), and SEQ ID NO: 3 (Vacc-13) over a period of 1-12 weeks; and
   b) a subsequent viral reactivation phase consisting of administering over a period of 1-4 consecutive weeks of an effective amount of 1-9 doses of Romidepsin at least 1-4 weeks after said therapeutic HIV-1 immunization phase;
   wherein an adjuvant, is administered in conjunction with, prior to, or simultaneously with said therapeutic HIV-1 immunization phase, and
   wherein the latent HIV-1 reservoir size is reduced in said subject following said therapeutic HIV-1 immunization phase and said viral reactivation phase.

2. The method according to claim 1, wherein said adjuvant, is recombinant human granulocyte-macrophage colony-stimulating factor (rhuGM-CSF).

3. The method according to claim 1, wherein the viral reactivation phase includes the administration of 1-8 doses, 1-7 doses, 1-6 doses, 1-5 doses, 1-4 doses, 1-3 doses, or 3 doses of an effective amount of Romidepsin.

4. The method according to claim 1, wherein step a) and/or b) are independently repeated 1, 2, 3, 4, 5, 6, 7, 8, 9, or 10 times in any order.

5. The method according to claim 4, wherein romidepsin is administered by infusions at a dose selected from a dose of between 2.5 mg/m2 and 7.5 mg/m2.

6. The method according to claim 1, wherein reduction of the HIV-1 latent reservoir size is in HIV-infected patients virologically suppressed on cART.

7. The method according to claim 1, wherein each peptide is given in a dose selected from 0.1-5 mg per administration.

8. The method according to claim 1, wherein the therapeutic HIV-1 immunization phase is over a period of 2-12 weeks.

9. The method according to claim 1, wherein the therapeutic HIV-1 immunization phase includes the administration of a number of doses selected from 1-10 doses, 2-10 doses, 3-10, 4-10, or 5-10 doses.

10. The method according to claim 1, wherein said four peptides are in the form of an acetate salt.

11. The method according to claim 1, wherein all four peptides are used in the ratio of 1:1:1:1 w/w.

12. The method according to claim 1, wherein said four peptides are in a dissolved liquid state, such as in water.

13. The method according to claim 1, which method further comprises the administering of one or more further therapeutically active agents selected from an immunomodulatory compound and a reservoir purging agent other than Romidepsin.

14. The method according to claim 13, wherein the immunomodulatory compound is selected from MDX-1106, thalidomide, anti-PD1 antibodies, cyclophosphamide, Levamisole, lenalidomide, CC-4047 (pomalidomide), CC-11006, and CC-10015.

15. The method according to claim 13, wherein the reservoir purging agent is selected from M344 (4-(dimethylamino)-N-[7-(hydroxyamino)-7-oxoheptyl]benzamide), chidamide (CS055/HBI-800), 4SC-202, (4SC), Resminostat (4SC), hydroxamic acids; benzamides, cyclic tetrapeptides, the depsipeptides, electrophilic ketones, the aliphatic acid compounds; compounds that activate transcription factors; Compounds that activate HIV mRNA elongation; IL-7; T-cell stimulating factors; Kinase inhibitors; PTEN (phosphatase and tensin homologue) gene inhibitors, Disulfiram (DSF), an inhibitor of acetaldehyde dehydrogenase, Protein Tyrosine Phosphatase Inhibitors, Toll-like receptors agonists, quercetin, lipoic acid, sodium butyrate, TNF-alpha, PHA and Tat.

16. A method for initiating a cell-mediated immune response in a subject infected with human immunodeficiency virus type 1 (HIV-1), the method comprising the steps of:
   a) a therapeutic HIV-1 immunization phase consisting of administering in one or more doses of an effective amount of at least four HIV-specific peptides comprising the amino acid sequences SEQ ID NO: 18 (Vacc-10), SEQ ID NO: 11 (Vacc-11), SEQ ID NO: 6 (Vacc-12), and SEQ ID NO: 3 (Vacc-13) over a period of 1-12 weeks; and
   b) a subsequent viral reactivation phase consisting of administering over a period of 1-4 consecutive weeks of an effective amount of 1-9 doses of Romidepsin at least 1-4 weeks after said therapeutic HIV-1 immunization phase;
   wherein an adjuvant, is administered in conjunction with, prior to, or simultaneously with said therapeutic HIV-1 immunization phase, and
   wherein a cell-mediated immune response is initiated in said subject.

17. The method of claim 16, wherein said cell-mediated immune response is measured by a delayed-type hypersensitivity skin reaction.

* * * * *